US012564734B2

(12) United States Patent
Wong et al.

(10) Patent No.: US 12,564,734 B2
(45) Date of Patent: Mar. 3, 2026

(54) ULTRA-HIGH DOSE RATE X-RAY CABINET IRRADIATOR

(71) Applicant: The Johns Hopkins University, Baltimore, MD (US)

(72) Inventors: John Wai-Chiu Wong, Baltimore, MD (US); Mohammad Rezaee, Baltimore, MD (US); Iulian Iordachita, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 192 days.

(21) Appl. No.: 18/032,137

(22) PCT Filed: Oct. 15, 2021

(86) PCT No.: PCT/US2021/055294
§ 371 (c)(1),
(2) Date: Apr. 14, 2023

(87) PCT Pub. No.: WO2022/082055
PCT Pub. Date: Apr. 21, 2022

(65) Prior Publication Data
US 2023/0390587 A1      Dec. 7, 2023

Related U.S. Application Data

(60) Provisional application No. 63/092,991, filed on Oct. 16, 2020.

(51) Int. Cl.
*A61N 5/10* (2006.01)

(52) U.S. Cl.
CPC .... *A61N 5/1077* (2013.01); *A61N 2005/1091* (2013.01); *A61N 2005/1094* (2013.01); *A61N 2005/1095* (2013.01)

(58) Field of Classification Search
CPC ...................... A61N 5/1077; A61N 2005/1091
See application file for complete search history.

(56) References Cited

U.S. PATENT DOCUMENTS 5,870,697 A * 2/1999 Chandler ............. A61N 5/1031
378/65
9,044,604 B2 6/2015 Dirauf et al.
(Continued)

FOREIGN PATENT DOCUMENTS

EP           3097951 A1    11/2016
KR      10-2019-0022148 A     3/2019
WO      WO-2006086631 A2 *   8/2006 ........... A61N 5/1042

OTHER PUBLICATIONS

Fujita, JP 2010-017202 A and its English translation. (Year: 2010).*
(Continued)

*Primary Examiner* — Chih-Cheng Kao
(74) *Attorney, Agent, or Firm* — Venable LLP; Ryan T. Ward

(57) ABSTRACT

An x-ray irradiation system includes a first x-ray tube constructed and arranged to be able to irradiate an object with at least a portion of a first x-ray beam emitted from the first x-ray tube, and a second x-ray tube constructed and arranged to be able to irradiate the object with at least a portion of a second x-ray beam emitted from said second x-ray tube simultaneously with said first x-ray beam. The first and second x-ray tubes are arranged such that the first and second x-ray beams are incident on, and intersect within, the object at respective first and second oblique angles to define a target volume such that a dose rate is substantially uniform as prescribed within said target volume.

25 Claims, 19 Drawing Sheets

(56) References Cited

U.S. PATENT DOCUMENTS

| | | | |
|---|---|---|---|
| 2006/0153330 A1 | 7/2006 | Wong | |
| 2007/0086576 A1* | 4/2007 | Yang | A61B 6/06 |
| | | | 378/152 |
| 2008/0192892 A1 | 8/2008 | Dilmanian | |
| 2009/0093863 A1 | 4/2009 | Dilmanian | |
| 2010/0189221 A1* | 7/2010 | Eaton | G21K 5/02 |
| | | | 378/68 |
| 2010/0189222 A1 | 7/2010 | Eaton | |
| 2012/0163540 A1 | 6/2012 | Van der veen | |
| 2012/0199760 A1 | 8/2012 | Handa et al. | |
| 2015/0231413 A1 | 8/2015 | Grady | |
| 2016/0310763 A1 | 10/2016 | Grady et al. | |
| 2019/0022411 A1* | 1/2019 | Parry | A61N 5/1084 |
| 2023/0364443 A1* | 11/2023 | Smolle | A61N 5/062 |

OTHER PUBLICATIONS

Rezaee et al., "Ultrahigh dose-rate (FLASH) x-ray irradiator for pre-clinical laboratory research", Physics in Medicine & Biology, (Apr. 23, 2021), vol. 66, No. 9, 095006.

Montay-Gruel et al., "Long-term neurocognitive benefits of FLASH radiotherapy by reduced reactive oxygen species", PNAS, (May 28, 2019), vol. 116, No. 22, pp. 10943-10951.

Vozenin et al., "The advantage of FLASH radiotherapy confirmed in mini-pig and cat-cancer patients", Clin. Cancer Res., (Jan. 1, 2019) vol. 25, No. 1, pp. 35-42.

Wilson et al., "Ultra-high dose rate (FLASH) radiotherapy: Silver bullet or fool's gold?", Front. Oncol., (Jan. 17, 2020), vol. 9, Article 1563, (12 pages).

Montay-Gruel et al., "X-ray can trigger the FLASH effect: Ultra-high dose-rate synchrotron light source prevents normal brain injury after whole brain irradiation in mice", Radiother, Oncol, (2018), vol. 129, pp. 582-588.

U.S. DOE "Workshop on Ion Beam Therapy" (2013), Office of Science, Jan. 9-11, 2013, Summary Report, (34 pages). https://science.osti.gov/-/media/hep/pdf/accelerator-rd-stewardship/Workshop_on_Ion_Beam_Therapy_Report_Final_R1.pdf.

Vozenin ett al., "Biological Benefits of Ultra-High Dose Rate FLASH Radiotherapy: Sleeping Beauty Awoken", Clin. Oncol., (2019), vol. 31, pp. 407-415.

Favaudon et al., "Ultrahigh dose-rate FLASH irradiation increases the differential response between normal and tumor tissue in mice", Sci. Transl. Med., (Jul. 16, 2014), vol. 6, Issue 245ra93, (9 pages).

Fouillade et al., "FLASH Irradiation Spares Lung Progenitor Cells and Limits the Incidence of Radio-induced Senescence", Clin. Cancer Res., (2020), vol. 26, pp. 1497-1506.

Girdhani et al., " Abstract LB-280: FLASH: A novel paradigm changing tumor irradiation platform that enhances therapeutic ratio by reducing normal tissue toxicity and activating immune pathways", Cancer Res., (2019), vol. 79, (13 Suppl), (4 pages).

Diffenderfer et al., "Design, Implementation, and in Vivo Validation of a Novel Proton FLASH Radiation Therapy System", Int. J. Rad. Onc. Biol. Phys., (2020), vol. 106, No. 2, pp. 440-448.

Loo et al., "Delivery of ultra-rapid flash radiation therapy and demonstration of normal tissue sparing after abdominal irradiation of mice", Int. J. Rad. Onc. Biol. Phys., (2017), vol. 98, E16, (1 page).

Levy et al., "FLASH irradiation enhances the therapeutic index of abdominal radiotherapy for the treatment of ovarian cancer", bioRxiv [Preprint]. (2019), doi: 10.1101/2019.12.12.873414.

Simmons et al., "Reduced cognitive deficits after FLASH irradiation of whole mouse brain are associated with less hippocampal dendritic spine loss and neuroinflammation", Radiother. Oncol., (2019), vol. 139, pp. 4-10.

Montay-Gruel et al., "Irradiation in a flash: unique sparing of memory in mice after whole brain irradiation with dose rates above 100Gy/s", Radiother. Oncol., (2017), vol. 124, pp. 365-369.

Bourhis et al., "Clinical translation of FLASH radiotherapy: why and how?", Radiother. Oncol., (2019), vol. 139, pp. 11-17.

Hendry et al., "The Constant Low Oxygen Concentration in All the Target Cells for Mouse Tail Radionecrosis", Radiat. Res., (1982), vol. 92, pp. 172-181.

Field et al., "Effects of dose-rate on the radiation response of rat skin", Int. J. Radiat. Biol. Relat. Stud. Phys. Chem. Med. (1974), vol. 26, Issue. 3, pp. 259-267.

Bourhis et al., "Treatment of a first patient with FLASH-radiotherapy", Radiother. Oncol., (2019), vol. 139, pp. 18-22.

AAPM Annual Meeting, "FLASH Therapy—Current Status and the Way to the Clinic", SAM Therapy Scientific Symposium, (2020).

Jaccard et al., "High dose-per-pulse electron beam dosimetry: Commissioning of the Oriatron eRT6 prototype linear accelerator for preclinical use.", Med. Phys., (Feb. 2018), vol. 45, No. 2, pp. 863-874.

Schuler et al., "Experimental Platform for Ultra-high Dose Rate FLASH Irradiation of Small Animals Using a Clinical Linear Accelerator", Int. J. Rad. Onc. Biol. Phys., (2017), vol. 97, No. 1, pp. 195-203.

Patriarca et al., "Experimental Set-up for FLASH Proton Irradiation of Small Animals Using a Clinical System", Int. J. Rad. Onc. Biol. Phys., (2018), vol. 102, No. 3, pp. 619-626.

Colangelo et al., "The Importance and Clinical Implications of FLASH Ultra-High Dose-Rate Studies for Proton and Heavy Ion Radiotherapy", Rad. Res., (2020), vol. 193, No. 1, (5 pages).

Spitz et al., "An integrated physico-chemical approach for explaining the differential impact of FLASH versus conventional dose rate irradiation on cancer and normal tissue responses", Radiother. Oncol., (2019), vol. 139, pp. 23-27.

Wilson et al., "Revisiting the ultra-high dose rate effect: implications for charged particle radiotherapy using protons and light ions", Brit. J. Radiol., (2012), vol. 85, pp. e933-e939.

Karsch et al., "Toward ion beam therapy based on laser plasma accelerators", Acta Oncologica, (2017), vol. 56, No. 11, pp. 1359-1366.

Buonanno et al., "Biological effects in normal cell exposed to FLASH dose rate protons", Radiother. Oncol., (2019), vol. 139, pp. 51-55.

Durante et al., "Faster and safer? FLASH ultra-high dose rate in radiotherapy", Br. J. Radiol., (2018), vol. 91, (4 pages).

Maxim et al., "PHASER: A platform for clinical translation of FLASH cancer radiotherapy", Radiother. Oncol., (2019), vol. 139, pp. 28-33.

Bazalova-Carter et al., "On the capabilities of conventional x-ray tubes to deliver ultra-high (FLASH) dose rates", Med. Phys., (Dec. 2019), vol. 46, No. 12, pp. 5690-5696.

Varex Imaging, "RAD-44 Rotating Anode X-Ray Tube", Corp., Salt Lake City, UT. Catalog No. 133785-000 Rev A. (Sep. 2021), (6 pages) https://www.vareximaging.com/sites/default/files/datasheets/vic/RAD-44pds_0.pdf.

Beyreuther et al., "Radiobiological response to ultra-short pulsed megavoltage electron beams of ultra-high pulse dose rate", Int. J. Radiat. Biol., (2015), vol. 91, pp. 643-652.

Sharma et al., "Radiation dose to patients from X-ray radiographic examinations using computed radiography imaging system", J. Med. Phys., (2015), vol. 40, No. 1, pp. 29-37.

Sungita et al., "Diagnostic X-ray facilities as per quality control performances in Tanzania", J. Appl. Clinic. Med. Phys., (Fall 2006), vol. 7, No. 4, pp. 66-73.

Ma et al., "AAPM protocol for 40-300 kV x-ray beam dosimetry in radiotherapy and radiobiology", Med. Phys., (Jun. 2001), vol. 28, No. 6, pp. 868-893.

Ashraf M, Rahman M, Zhang R, Williams BB, Gladstone DJ, Pogue BW, Bruza Pet al., "Dosimetry for FLASH Radiotherapy: A Review of Tools and the Role of Radioluminescence and Cherenkov Emission", Front. Phys., (2020), vol. 8, Article 328, (20 pages).

Jaccard et al., "High dose-per-pulse electron beam dosimetry: Usability and dose-rate independence of EBT3 Gafchromic films", Med. Phys., (2017), vol. 44, pp. 725-735.

Agostinelli et al., "GEANT4—a simulation toolkit", Nucl. Instrum. Methods. Phys. Res. B., (2003), vol. 506, No. 3, pp. 250-303.

Bordage et al., "Implementation of new physics models for low energy electrons in liquid water in Geant4-DNA", Physica Medica., (2016), vol. 32, pp. 1833-1840.

(56) References Cited

OTHER PUBLICATIONS

Pandola et al., "Validation of GEANT4 simulation of bremsstrahlung from thick targets below 3 MeV", Nucl. Instrum. Methods. Phys. Res. B., (2018), vol. 350, pp. 41-48.

Patallo et al., "Development and Implementation of anEnd-To-End Test for Absolute Dose Verificationof Small Animal Preclinical Irradiation Research Platforms", Int. J. Rad. Onc. Biol. Phys., (2020), vol. 107, No. 3, pp. 587-596.

Wang et al., "Dosimetric verification and commissioning for a small animal image-guided irradiator", Phys. Med. Biol., (2018), vol. 63, (13 pages).

Bell et al., "Interleukin 6 Signaling Blockade Exacerbates Acute and Late Injury From Focal Intestinal Irradiation", Int. J. Rad. Onc. Biol. Phys., (2019), vol. 3, No. 1, pp. 719-727.

Verginadis et al., "A Novel Mouse Model to Study Image-Guided, Radiation-Induced Intestinal Injury and Preclinical Screening of Radioprotectors", Cancer Res., (Feb. 15, 2017), vol. 77, No. 4, pp. 908-917.

Kim et al., "Epithelial cell alpha3beta1 integrin links beta-catenin and Smad signaling to promote myofibroblast formation and pulmonary fibrosis", The Journal of Clinical Investigation, (Jan. 2009), vol. 119, No. 1, pp. 213-224.

Kim et al., "Alveolar epithelial cell mesenchymal transition develops in vivo during pulmonary fibrosis and is regulated by the extracellular matrix", PNAS, (Aug. 29, 2006), vol. 103, No. 35, pp. 13180-13185.

Wei et al., "Regulation of alpha5beta1 integrin conformation and function by urokinase receptor binding", The Journal of Cell Biology, (Jan. 31, 2005), vol. 168, No. 3, pp. 501-511.

Kim et al., "Endothelin-1 as Initiator of Epithelial-Mesenchymal Transition: Potential New Role for Endothelin-1 during Pulmonary Fibrosis", American Journal of Respiratory Cell and Molecular Biology, (2007), vol. 37, pp. 1-2.

Festing et al., "Guidelines for the Design and Statistical Analysis of Experiments Using Laboratory Animals", ILAR J, (2002), vol. 43, No. 4, pp. 244-258.

* cited by examiner

220

210

215

225

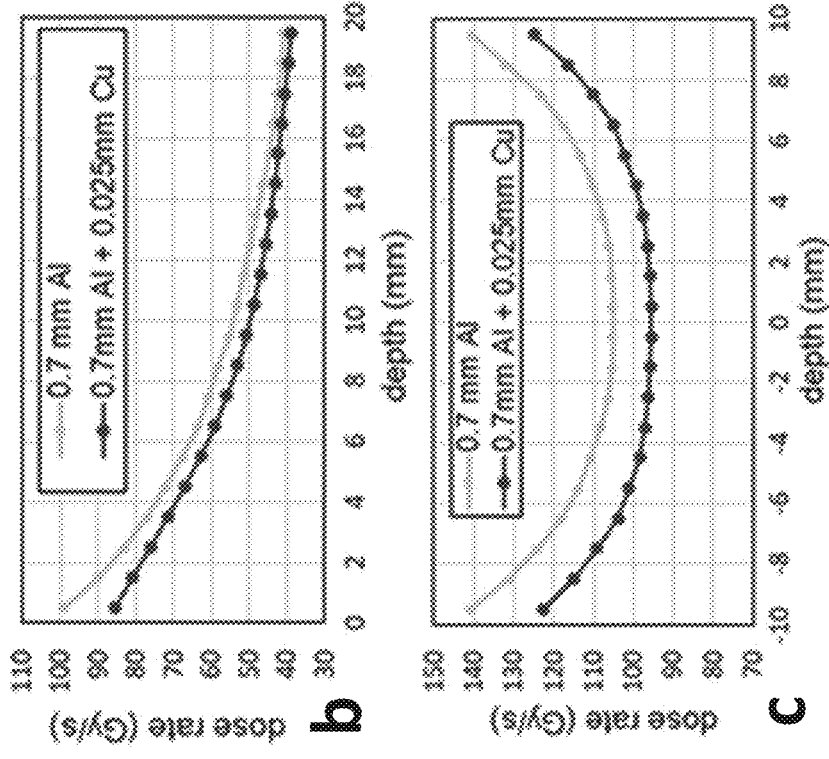
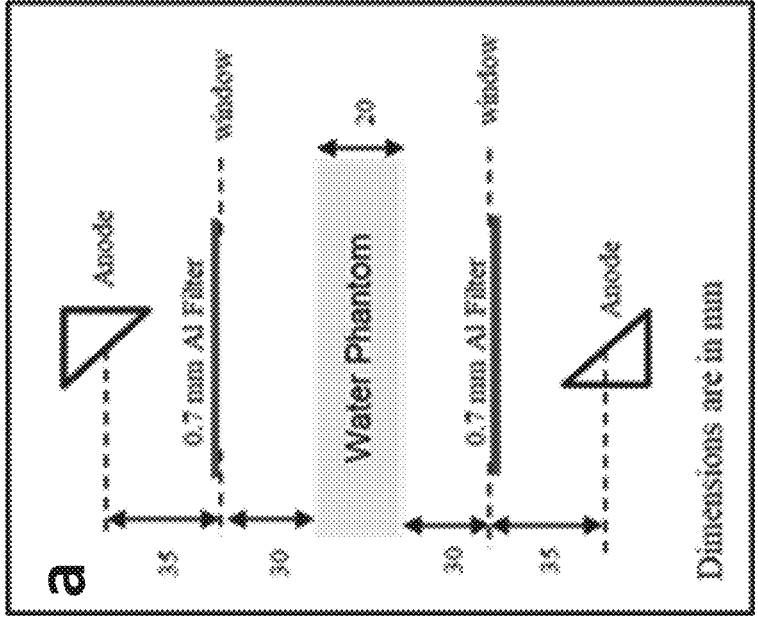
FIGS. 5A to 5C

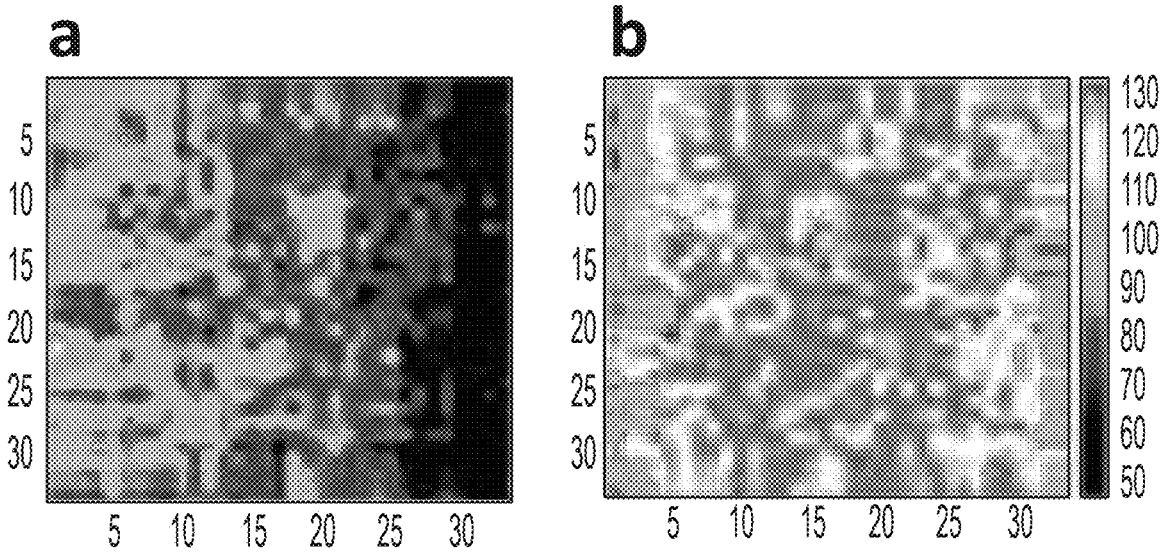
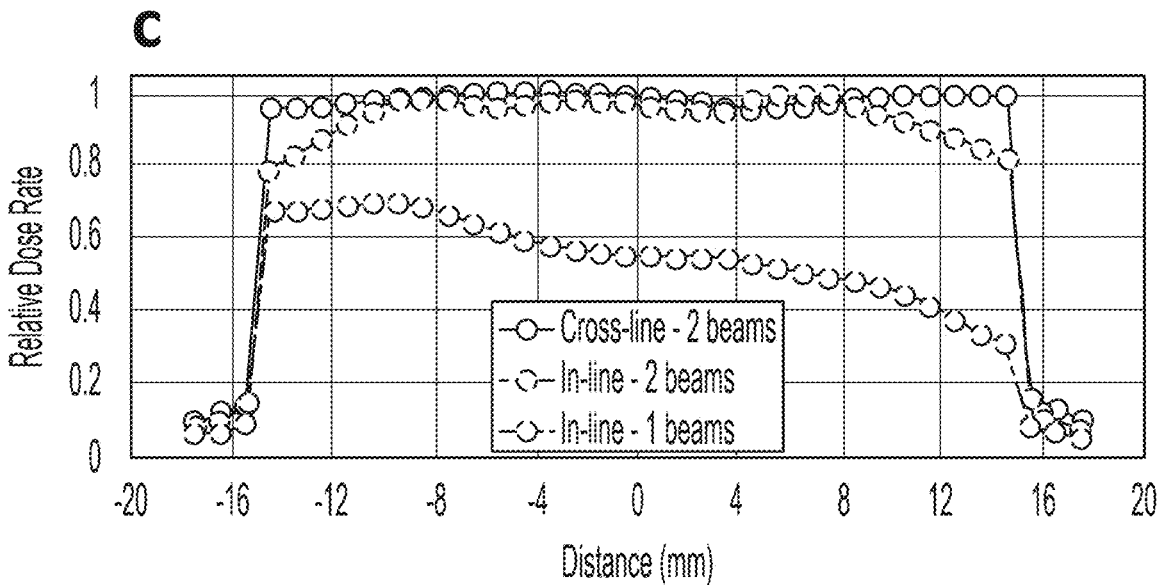
FIGS. 6A to 6C

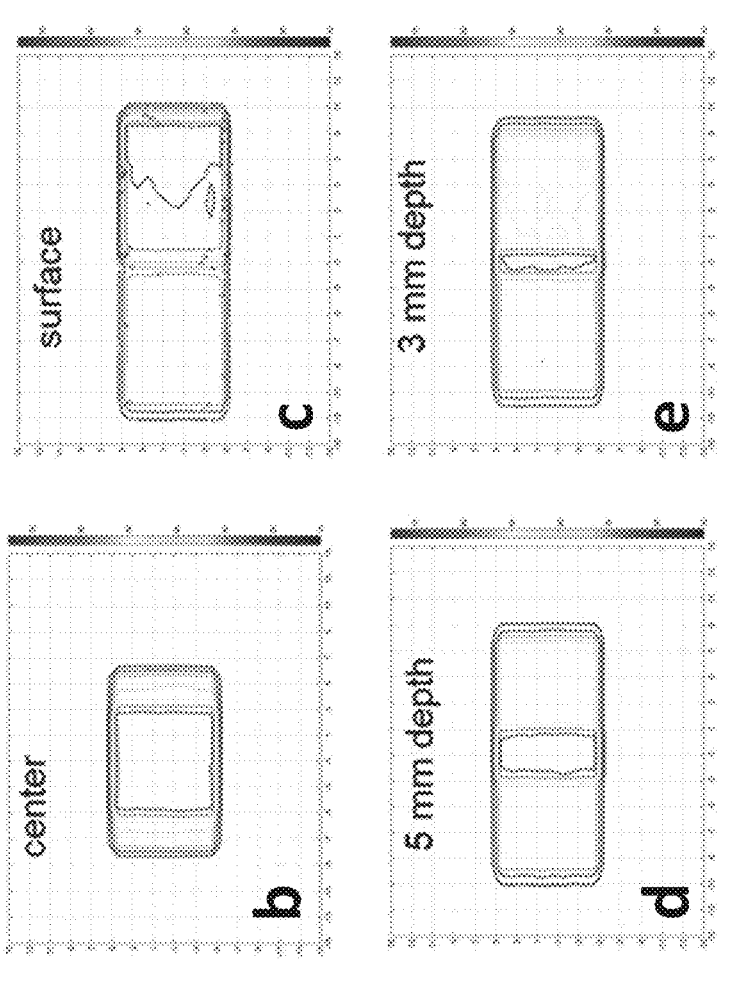
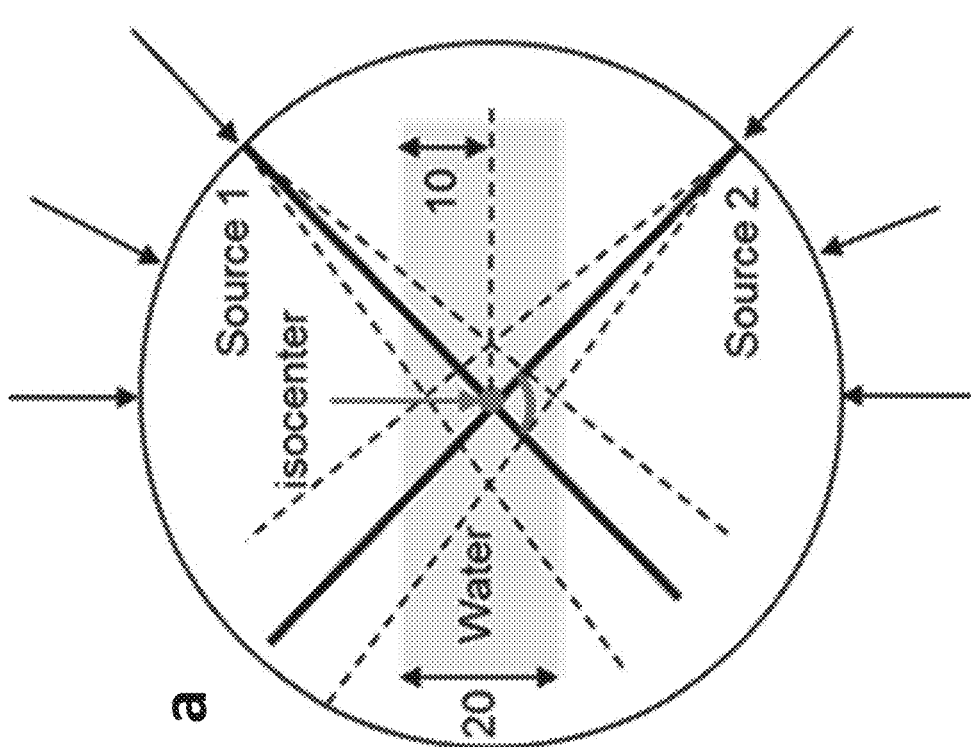
FIGS. 9A to 9E

Adaptor to dock irradiator 1210

1205

1205

Tabs to immobilize mouse by holding extremities/tail using rubber hands 1205

1205

1205

Polycarbonate mouse bed

Fiducial markers

1215

1200

ULTRA-HIGH DOSE RATE X-RAY CABINET IRRADIATOR

This application is a U.S. National Stage of PCT/US2021/055294, filed Oct. 15, 2021, which claims priority to U.S. Provisional Application No. 63/092,991, filed Oct. 16, 2020, which is incorporated herein by reference in its entirety.

BACKGROUND

1. Technical Field

Currently claimed embodiments of this invention relate to systems and methods for x-ray irradiation, and more particularly systems and methods for ultra-high dose rate (FLASH) radiotherapy.

2. Discussion of Related Art

FLASH radiotherapy, the delivery of high radiation dose (10-30 Gy and above) at ultra-high dose rates (40-200 Gy/s and above), has recently been shown [1-3] to reduce significantly normal tissue toxicity compared to conventional irradiation (0.05-0.4 Gy/sec), while maintaining tumor control probability at similar level. However, the biological mechanisms of FLASH irradiation (FLASH effect) are not well understood. The clinical translation of FLASH irradiation necessitates comprehensive laboratory studies to elucidate the biological effects as well as pertinent technological and physical requirements. FLASH has transformative potential to significantly enhance the efficacy of radiotherapy in cancer treatment.

In a recent Department of Energy (DOE) workshop on the challenges of particle therapy, the delivery of radiation at very high dose rates was suggested as a solution to mitigate the problem of organ motion [5, 6]. The notion was followed by reports that FLASH irradiation improved normal tissue sparing in laboratory animals. An increasing number of preclinical studies ensued on the toxicities in the thorax [8-10], abdomen [11-13], brain [1,4,14-16], skin [17,18], including Zebra fish embryos [7]. In majority of the preclinical studies, FLASH effects were observed at the dose rates and doses in the ranges of 40-200 Gy/s and 10-30 Gy, respectively. FLASH effects have also been observed in larger animals such as cat and pig, resulting in minimal acute and late normal tissue toxicities, with no changes in tumor response between FLASH and conventional irradiations [2]. In France, the first human patient with recurrent cutaneous T-cell lymphoma was successfully treated with electron FLASH radiotherapy [19]. The promising results generate great excitement for a potential major breakthrough in cancer treatment, as evident in the spike of FLASH research activities in the community [20-22] and the significant investment of the technology industry in sponsoring international research consortia on FLASH radiotherapy (Varian Palo Alto, IBA Louvain-la-Neuve, IntraOP Sunnyvale).

At present, studies of FLASH effects rely predominantly on high energy particles, mainly 4-9 MeV electrons and 100-230 MeV protons, produced at or near clinical treatment facilities [3]. FLASH effects using 100 keV x-rays from a specialized synchrotron have also been reported [4]. All these radiations are produced by complex accelerators of limited availability to the laboratory researchers. The much-promoted proton beams are available only at selected proton treatment centers worldwide. Machine accessibility and its distance from the laboratory, with a few exceptions, pose significant logistical challenges to the customary practice of preclinical radiation research. Ultra-high dose rate electron beams of 4-10 MeV from dedicated [23] or modified clinical accelerators [24] are particularly attractive for FLASH irradiation research on small animals. However, their propensity of substantial scattering and spreading renders them less suitable for normal tissue toxicity studies with small laboratory animal tumor models where localized irradiation is imperative.

FIGS. 1A and 1B show a GEANT4 Monte Carlo (MC) simulation of 2D dose distribution in a 20-mm thick water phantom, from 1 mm×1 mm (FIG. TA) and 5 mm×5 mm (FIG. 1B) non-diverging planar square fields of 4 MeV electrons, 6 MeV electrons, and 150 kVp x-rays impinging on a water medium (infinite SSD, beam direction as indicated). For the electron irradiation, a substantial volume of the medium received lower doses outside the central region where dose uniformity is maintained. The effects of electron dose spread have not been evaluated in current FLASH studies as the focus is on whole organ or superficial lesions, and warrant attention where toxicity of adjacent normal tissue is of concern. In contrast, x-ray distribution shows minimal lateral spread indicative of local energy deposition at the 150 kVp energy. The undesirable feature of the kV x-ray beam is the steep dose gradient, decreasing by more than 50% at 10 mm depth.

The use of proton beams for FLASH research has garnered much attention as the requisite high dose rates are readily achieved with proton pencil beams from the current generation of proton accelerators [11,25]. However, in some instances, scan times for even small field size of 10 mm×10 mm reduce dose rate and necessitate the use of passive scattering technique [25], where the resultant lateral dose spread will be of concern [11]. More importantly, the use of proton beams raises questions on the relationship of LET with the emergent hypothesis of FLASH-induced oxygen depletion in reducing radiation injury [3,26-28]. It has been reported that FLASH effects would be negligible with high LET irradiation as the associated cellular damage is less sensitive to oxygen in the environment [3,29,30]. Consequently, current studies of proton FLASH effects have been limited to the plateau region where the LET distribution is low and relatively homogeneous [11,25].

Clearly, the relationship of LET and FLASH effects needs to be elucidated and will need to include the use of photons, electrons, protons, and ions [26-28,31]. These findings will be of utmost importance in driving the development of next generation of medical accelerator as envisioned by the DOE [5]. For clinical FLASH treatment, other major challenges will certainly arise and must be addressed. One notable development is the concept of PHASER system consisting of multiple stationary 6 MV x-ray sources on a ring gantry to overcome the need of inherently slow mechanical motion of present conformal treatment [32]. Similarly, the capability of low-LET photons and electrons to treat deep-seated tumors needs to be leveraged. It follows then, fundamental mechanistic research on FLASH irradiation in the laboratory must incorporate low LET radiation, in particular, commonly used kV x-rays. Strikingly, other than one study with the exquisite synchrotron x-rays [4], kV x-rays have not been employed in any of FLASH research to date.

Self-shielded kV x-ray cabinet systems are staple instruments for preclinical laboratory research. It would be ideal to extend the capabilities of current x-ray irradiators to support FLASH irradiation of small animals. At present, all cabinet irradiators are based on x-ray sources with stationary anode technology. A recent study showed that commercially available 160 and 165 kVp sources with stationary anode can produce x-rays at the FLASH dose rates of 100-150 Gy/s at the tube exit window [33]. The dose rates, however, decreased rapidly below 20 Gy/s within a few millimeter distances from the exit window, which made them unsuitable for preclinical research on small animals.

Accordingly, there is a clear compelling need of a preclinical self-shielded kVp x-ray cabinet system capable of achieving 10-50 Gy doses at the dose rates of 40-200 Gy/s with depth-dose uniformity and field dimensions that are sufficient for the irradiation of murine models. Making FLASH irradiation broadly available to the research community is critical to advance the research and translation of FLASH radiotherapy.

SUMMARY

An x-ray irradiation system, including a first x-ray tube constructed and arranged to be able to irradiate an object with at least a portion of a first x-ray beam emitted from said first x-ray tube, and a second x-ray tube constructed and arranged to be able to irradiate said object with at least a portion of a second x-ray beam emitted from said second x-ray tube simultaneously with said first x-ray beam. The first and second x-ray tubes are arranged such that said first and second x-ray beams are incident on, and intersect within, the object at respective first and second oblique angles to define a target volume such that a dose rate is substantially uniform as prescribed within said target volume.

A method for x-ray irradiation, including arranging a first x-ray tube to irradiate an object with at least a portion of a first x-ray beam emitted from said first x-ray tube, and arranging a second x-ray tube to irradiate said object with at least a portion of a second x-ray beam emitted from said second x-ray tube simultaneously with said first x-ray beam. The first and second x-ray tubes are arranged such that said first and second x-ray beams are incident on, and intersect within, the object at respective first and second oblique angles to define a target volume such that a dose rate is substantially uniform as prescribed within said target volume.

BRIEF DESCRIPTION OF THE DRAWINGS

Further objectives and advantages will become apparent from a consideration of the description, drawings, and examples.

FIGS. 5A-5C show a schematic of parallel-opposed setup with mirrored beams to offset the heel effect, and the corresponding depth dose-rate curves in the water phantom.

FIGS. 6A-6C show cross-beam dose-rate distributions in the central slice of the phantom from single and opposing pair of the x-ray sources using the external Cu filter.

FIGS. 9A-9F illustrate beam angling for a pair of x-ray sources to minimize high entrance and exit doses to a 20-mm thick water phantom.

DETAILED DESCRIPTION

Figures 1A, 1B:
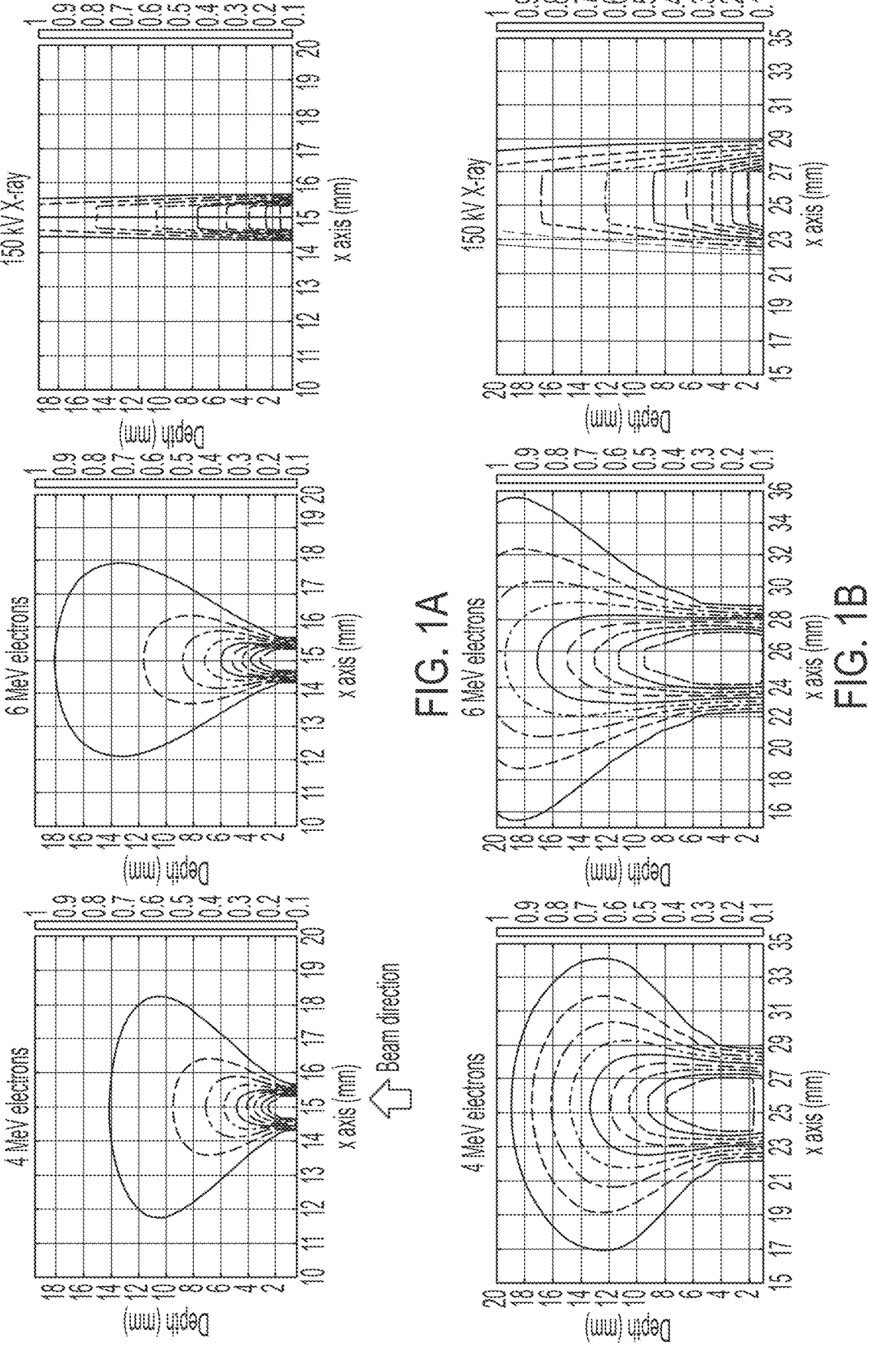
FIGS. 1A and 1B show Monte Carlo simulations of 2D dose distribution.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed, and other methods developed, without departing from the broad concepts of the current invention. All references cited anywhere in this specification, including the Background and Detailed Description sections, are incorporated by reference as if each had been individually incorporated.

Some embodiments provide a self-shielded x-ray irradiation system that greatly enhances basic and translational researches in the laboratory setting. The system includes a first x-ray tube constructed and arranged to be able to irradiate an object with at least a portion of a first x-ray beam emitted from the first x-ray tube, and a second x-ray tube constructed and arranged to be able to irradiate the object with at least a portion of a second x-ray beam emitted from the second x-ray tube simultaneously with the first x-ray beam. The first and second x-ray tubes are arranged such that said first and second x-ray beams are incident on, and intersect within, the object at respective first and second oblique angles to define a target volume such that a dose rate is substantially uniform as prescribed within the target volume, and avoiding overlap of the incident beams at the surfaces of the object.

In some embodiments, the first and second x-ray tubes are arranged in a mirrored orientation to minimize an inherent non-uniform emission of x-rays from each x-ray tube. In various embodiments, at least one of the x-ray tubes may include a rotating anode, and at least one of the x-ray tubes may be actively cooled.

The x-ray irradiation system may also include a positioning assembly to which the first and second x-ray tubes are attached, such that the first and second x-ray tubes are further arranged at respective first and second vertical positions on the positioning assembly. The angle of at least one x-ray source is adjustable on the positioning assembly to irradiate the treatment volume with an x-ray beam at a range of angles from –90 to 90 degrees, as measured from a vertical axis parallel to the vertical structure. In addition, the vertical position of at least one x-ray tube is adjustable on the positioning assembly to irradiate the treatment volume with an x-ray beam at a range of source to surface distances (SSDs) from zero to 250 millimeters (mm), as measured from a surface of the object to the aperture of the x-ray tube.

In some embodiments, based on the vertical position and angle of at least one x-ray tube, the dose rate in the target volume is an ultra-high dose rate between 40 Gy/sec to 200 Gy/sec. In some embodiments, based on the vertical position and angle of at least one x-ray tube, the dose rate in the target volume is a conventional dose rate between 0.02 Gy/sec to 0.4 Gy/sec. In some embodiments, based on the vertical position and angle of at least one x-ray tube, the dose rate in the target volume can be continually adjusted to achieve between 0.02 Gy/sec to 200 Gy/sec.

In some embodiments, the system provides both FLASH and conventional dose rates in the range of 0.02-200 Gy/s with absolute doses up to 67 Gy in a 2-cm thick water phantom, which represents small animals such as mice.

In some embodiments, the x-ray irradiation system also includes a sample holder positioned between the first x-ray tube and the second x-ray tube. The object to be irradiated is positioned within the sample holder. The object may be a biological sample or a living animal.

In some embodiments, the x-ray irradiation system also includes a filter coupled to an aperture of each x-ray tube, the filter being configured to modify at least one of energy spectrum, flatness, and symmetry of the emitted x-ray beams. The filter may be constructed of at least one of aluminum, beryllium, tin, copper, brass, tungsten, and alloys.

In some embodiments, the x-ray irradiation system also includes a collimator coupled to an aperture of each x-ray tube, the collimator being configured to shape the x-ray beam during irradiation of the target volume.

In some embodiments, the x-ray irradiation system also includes a non-transitory machine-readable medium storing a set of instructions for performing Monte Carlo-based dose calculations of the irradiated target volume, the calculations including calculating at least one of delivered dose, dose rate, Linear Energy Transfer (LET), and resultant chemical radicals distributions.

In some embodiments, the x-ray irradiation system also includes a third x-ray tube constructed and arranged to be able to irradiate said object with at least a portion of a third x-ray beam emitted from the third x-ray tube simultaneously with the first and second x-ray beams, the third x-ray tube being arranged such that said third x-ray beam is incident on, and intersects, the first and second x-ray beams within the object at a third oblique angle to further define the target volume such that the dose rate is substantially uniform within said target volume.

In some embodiments, at least one x-ray tube may be operated at a max peak voltage between 50 kilovolts (kV) and 320 kV, at a current between 5 milliamperes (mA) and 1000 mA, and/or for an exposure time between 50 milliseconds (msec) and 1000 msec. In some embodiments, at least one x-ray tube is one of a radiographic x-ray tube, a fluoroscopic x-ray tube, an angiographic x-ray tube, and a tomographic x-ray tube.

In some embodiments, the x-ray irradiation system also includes a self-shielded cabinet with an environmental control system.

Some embodiments provide a method for x-ray irradiation, that includes arranging a first x-ray tube to irradiate an object with at least a portion of a first x-ray beam emitted from the first x-ray tube, and arranging a second x-ray tube to irradiate the object with at least a portion of a second x-ray beam emitted from the second x-ray tube simultaneously with the first x-ray beam. The first and second x-ray tubes are arranged such that said first and second x-ray beams are incident on, and intersect within, the object at respective first and second oblique angles to define a target volume such that a dose rate is substantially uniform as prescribed within the target volume.

In some embodiments, the method includes arranging at least one x-ray tube at a vertical position and angle relative to the object such that the dose rate in the target volume is an ultra-high dose rate between 40 Gy/sec to 200 Gy/sec. In some embodiments, the method includes arranging at least one x-ray tube at a vertical position and angle relative to the object such that the dose rate in the target volume is a conventional dose rate between 0.02 Gy/sec to 0.4 Gy/sec.

An embodiment of the invention with an opposing pair of x-ray sources is shown in FIGS. 2A-2G. This example is a cabinet system 200 that is fully enclosed by a self-shielded cabinet 205, with rolling casters 207 for mobility, and incorporating at least an opposing pair of rotating anode kV x-ray sources 210, 215, capable of delivering irradiations at FLASH (40-200 Gy/s) and conventional (0.05-0.4 Gy/s) dose rates for preclinical (e.g. mouse) laboratory research. The first order specifications of the cabinet system 200 include providing radiation that (a) penetrates a 20-mm thick medium (equivalent to a mouse thickness) to achieve an adequate uniform depth dose (±5%) over 10 mm, (b) delivers an absolute dose up to 50 Gy at FLASH dose rates of 40-200 Gy/s in the irradiated volume, and (c) irradiates a 30 mm×15 mm field covering a half torso of a mouse. The system is capable of off-axis positional adjustments of the two x-ray sources 210, 215 to enable conformal irradiation and uniform dose rates at depth. In some embodiments, three or more x-ray sources are used with three-dimensional positioning.

In this example, the cabinet system 200 uses a pair of parallel opposed, actively cooled, x-ray sources 210, 215 with rotating anodes, such as those typically used for high frame rate fluoroscopic imaging purposes. The parallel-opposed x-ray sources 210, 215 are supported on a vertical structure 220, with a sample holder 225 (e.g., a plate) to support a laboratory subject (e.g., small animal, or cell culture plates) placed at mid-point (i.e., isocenter) between the two x-ray sources 210, 215 for irradiation.

The proximity of the x-ray sources 210, 215 to each other and to the subject can be altered, under manual or motorized control, to facilitate adjusting the effective dose rate at the mid-plane between them. A control system, such as a computerized control system, for the position of the x-ray sources may be integrated into the base of the system cabinet 200. The x-ray sources 210, 215 may be arranged in a parallel-opposed orientation. Furthermore, the parallel-opposed x-ray sources 210, 215 may also be arranged in a mirrored orientation to alleviate inherent non-uniform emission from each source (i.e., the heel effect). In some embodiments, the vertical structure 220 supporting the two x-ray sources 210, 215 can be operated in continuous or step-wise rotation mode under computer control.

Filters 230 of appropriate material composition can be placed at the emission window of each x-ray source to adjust the energy spectrum, the flatness, and the symmetry of the emitted x-ray beams. Adjustable or fixed collimators (not shown) may also be placed at the emission window of each x-ray source to allow appropriate shaping of the beam apertures for irradiation.

The x-ray sources 210, 215 can be employed in some embodiments to produce radiographic images on a digital imaging plate (not shown), for guidance purposes, of the irradiated subject in conjunction with the beam aperture. The cabinet system 200 functions in some embodiments as an improvement of existing kVp x-ray-based laboratory irradiation systems and as a replacement for radioisotope-based systems.

A radiation treatment planning system may also be available to provide the necessary irradiation settings of the sources to achieve the dose and dose rate to be delivered as desired, and to display 3D dose distribution in the irradiated subject. In some embodiments, the treatment planning system is a Monte-Carlo based dose calculation system to provide information on the delivered dose, dose rate, LET, and resultant chemical radicals distributions in the irradiated target, pertinent to FLASH research.

Some embodiments of the invention use a RAD-44 (Varex Imaging Corp.), a high capacity radiographic and fluoroscopy tube with a rotating anode [34] for each x-ray source. RAD-44 has a 16-degree rhenium-tungsten molybdenum target with two focal spots of 1.0 and 2.0 mm and nominal powers of 55 and 115 kW. The x-ray tube operates at the peak voltage of 150 kV. The RAD-44 has 0.7 mm Aluminum (Al) inherent equivalent filter. The tube operates in either radiographic or fluoroscopic modes to deliver radiation dose in a single or multiple pulses, respectively. This allows investigation of the uncertain relationship of pulse dose-rate with FLASH effects [7,35].

Other potential components of the invention in some embodiments include at least one of an adjustable irradiation chamber with an environmental control system (e.g., 0.1-21% O2), various fixed beam apertures (e.g., 5-30 mm) and filters, and flat panel imaging for sample positioning and localization (either digital or film).

As required for medical imaging, each rotating anode x-ray source, opposite to a stationary anode, can be turned on instantaneously with less than 5% uncertainty in time and exposure [36-38]. A control system is implemented to operate the two sources in synchrony, or independently, as desired for the study. The control system may be stored in the base of the system cabinet 200, or alternatively may be external to the system cabinet 200, with wired or wireless communication to the x-ray source hardware. For FLASH irradiation, anode heat loading will be in the range of 9-35 kJ in each tube to deliver 10-50 Gy at the dose rates of 40-200 Gy/s to a 20-mm thick water phantom. The heat is within 12% of maximum anode system with parallel-opposed heat tolerance of 300 kJ for the tube. Exposure time for the FLASH-irradiation is expected to be within 75-500 ms.

Figure 2B:
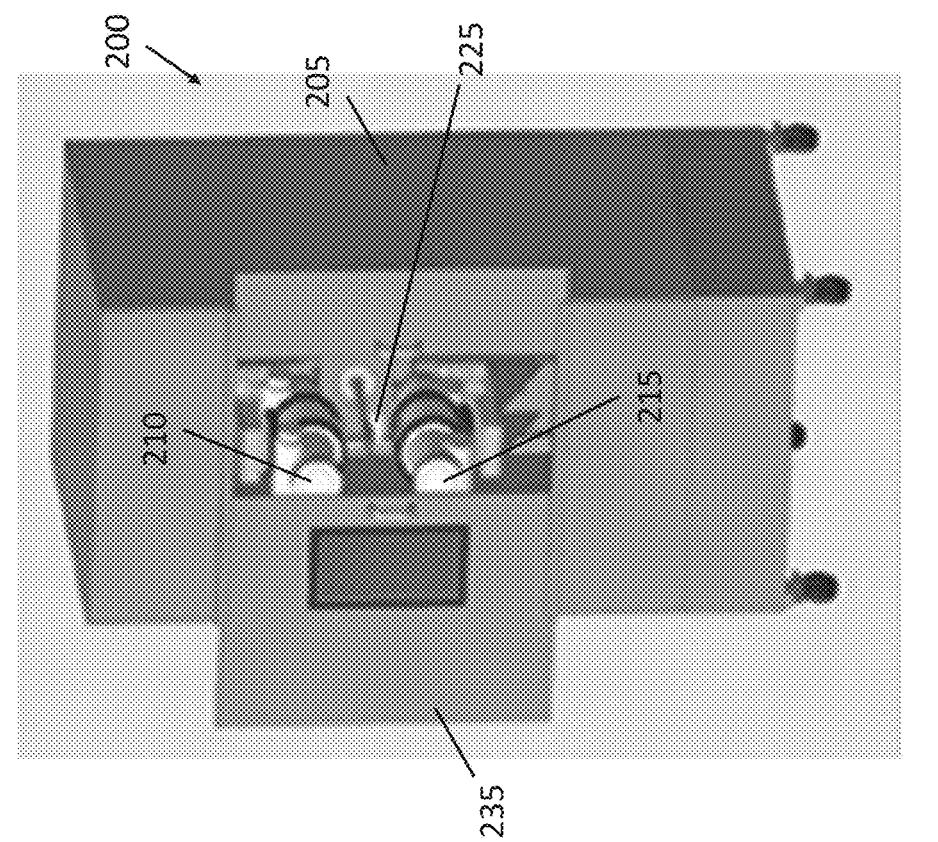
FIG. 2B shows a mode for FLASH irradiation.
Figure 2A:
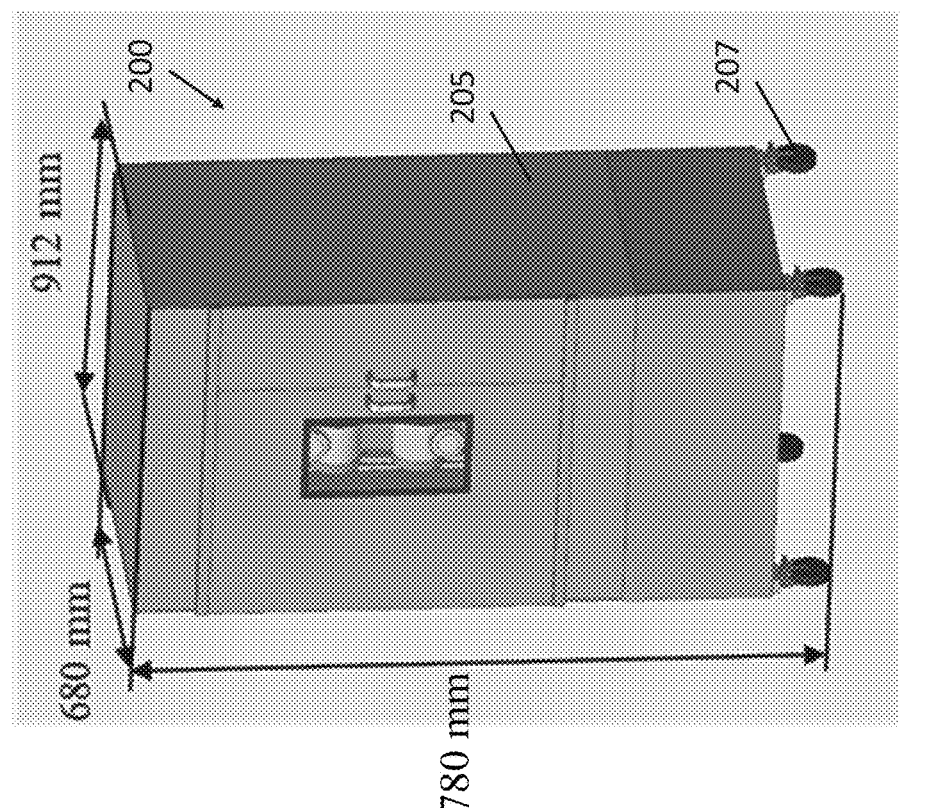
FIG. 2A illustrates an example of size measurements of a self-shielded cabinet in some embodiments.

FIG. 2A illustrates an example of size measurements of a self-shielded cabinet 205 in some embodiments. Specifically, in this example, the cabinet 205 is 1.78 meters tall (including rolling casters 207 for moving the cabinet), 0.68 meters deep, and 0.912 meters wide. While the measurements are given for the purpose of illustration, the actual size of the cabinet 205 may vary depending on accommodation requirements for the x-ray tubes, cooling, shielding, and geometry, especially in embodiments with more than two x-ray sources and different geometries.

Figure 2D:
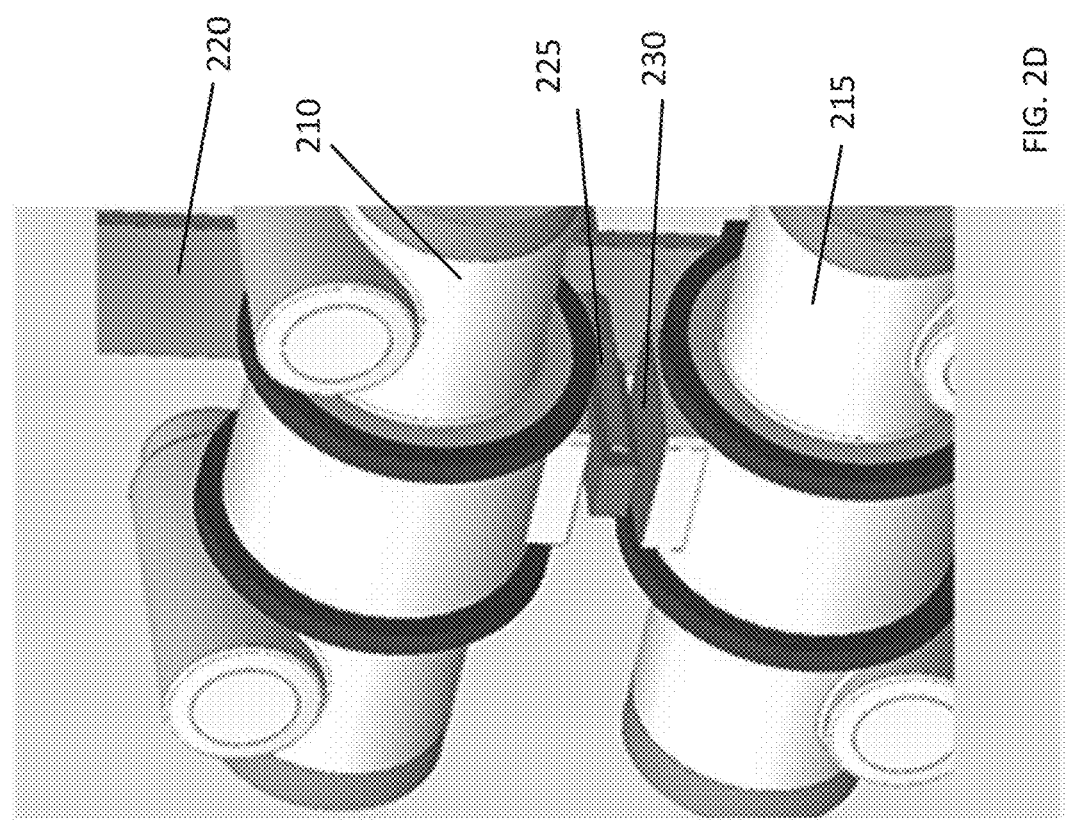
FIG. 2D shows a detail view of the mode in FIG. 2C, with the cabinet omitted for clarity.
Figure 2C:
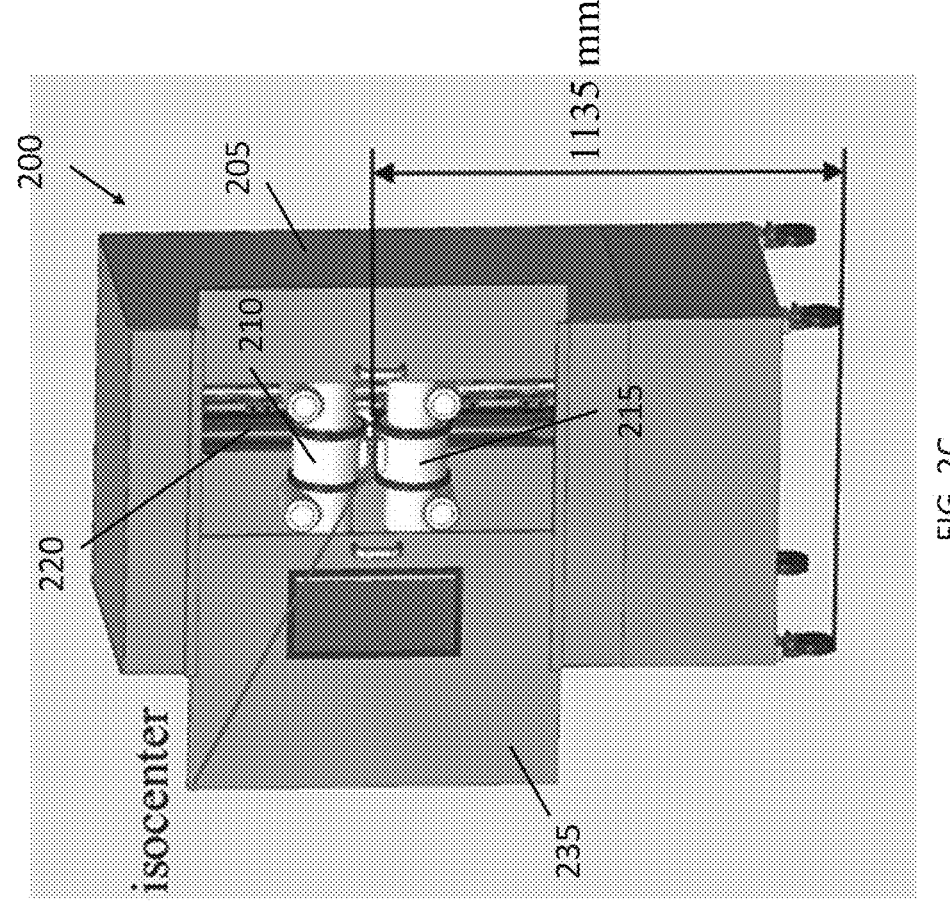
FIG. 2C shows an alternate mode for FLASH irradiation, where the x-ray sources are rotated.

FIGS. 2B-2D illustrate multiple views of different embodiments of the self-shielded cabinet system 200, with different arrangements of the x-ray sources 210, 215. FIG. 2B shows a mode for FLASH irradiation where the x-ray sources 210, 215 are positioned close to the sample holder 225. FIG. 2C shows an alternate mode for FLASH irradiation, where the x-ray sources 210, 215 are orthogonally rotated by 90 degrees. The isocenter of the two x-ray beams is 1.135 meters from the floor in this example. FIG. 2D shows a detail view of the mode in FIG. 2C, with the cabinet 205 omitted. The x-ray sources 210, 215 are mounted to the vertical structure 220 in the rotated configuration, with the sample holder 225 between them. The filter 230 on the bottom x-ray source 215 is also visible in this view.

Figure 2F:
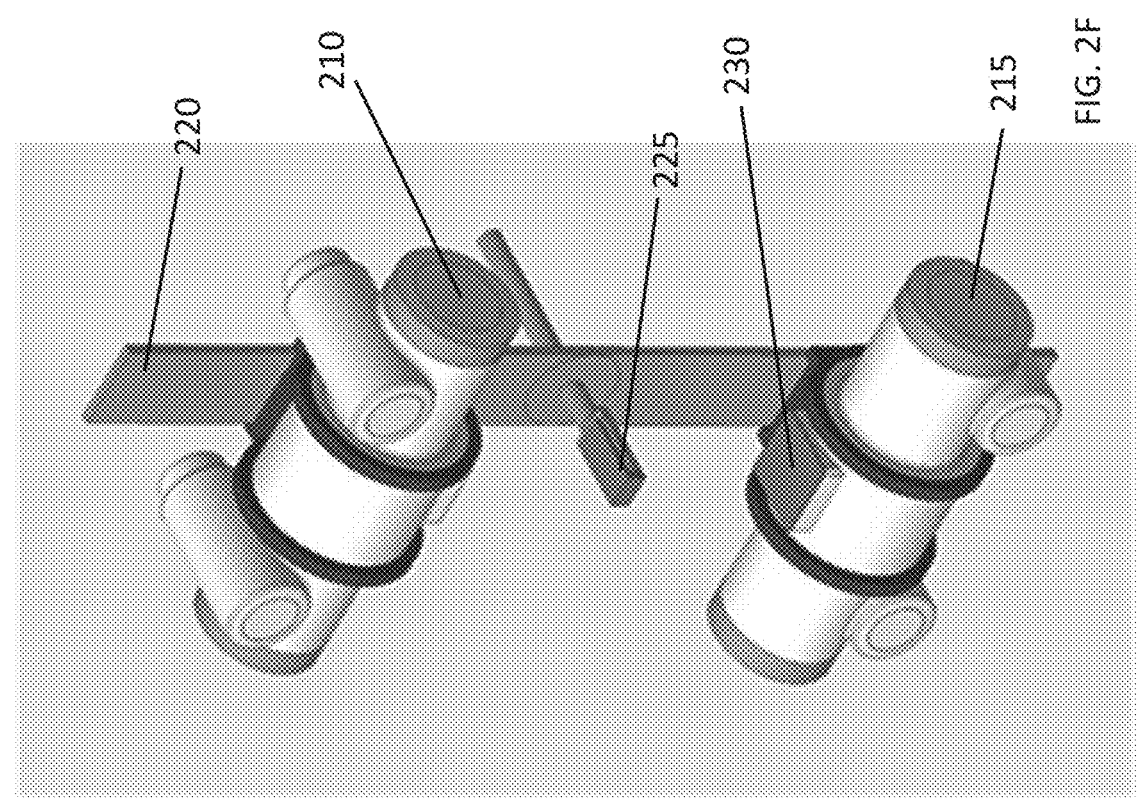
FIG. 2F shows a detail view of the mode in FIG. 2E, with the cabinet omitted for clarity.
Figure 2E:
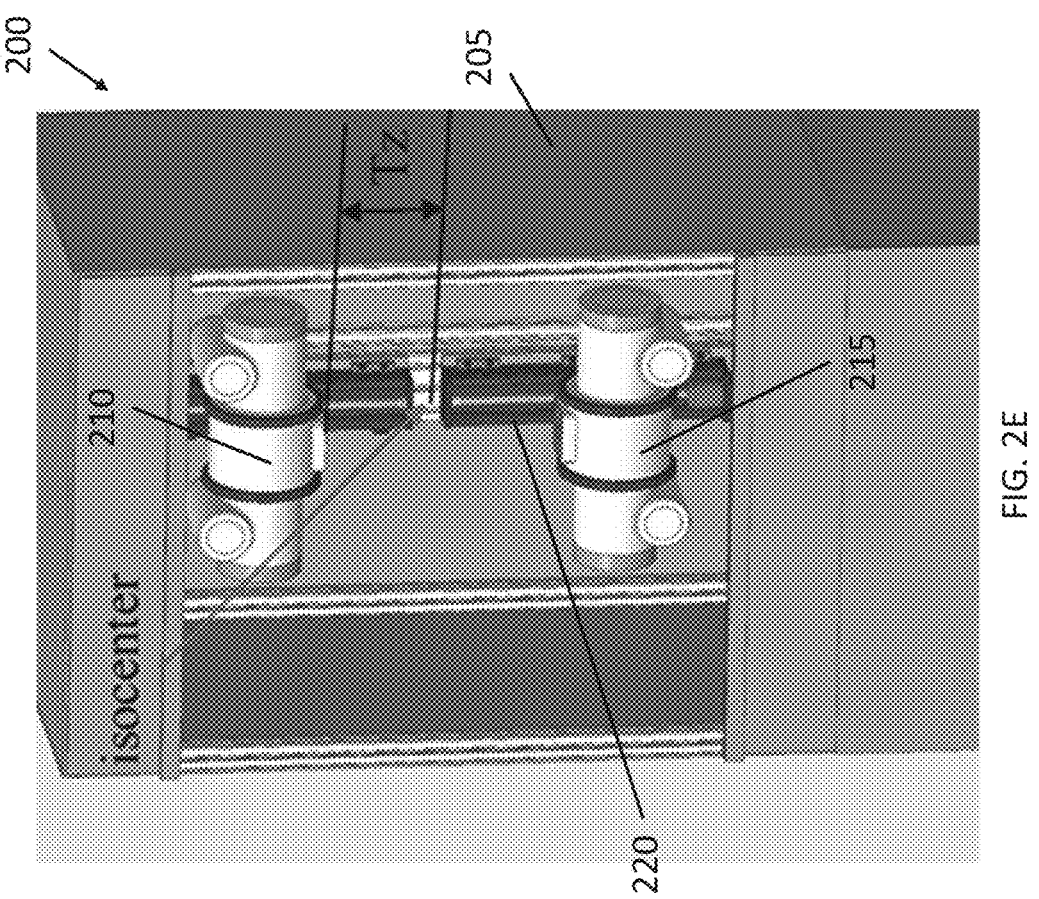
FIG. 2E shows a mode for conventional irradiation, with the cabinet door omitted for clarity.

FIG. 2E shows a mode for conventional irradiation, with the cabinet door 235 omitted for clarity. In this mode, the x-ray sources 201, 215 are positioned farther apart from the sample holder 225, with a distance Tz between the isocenter and the x-ray source. FIG. 2F shows a detail view of the mode in FIG. 2E, with the cabinet 205 omitted. The x-ray sources 210, 215 are mounted to the vertical structure 220 in the same rotated configuration as the mode in FIGS. 2C and 2D, with the sample holder 225 between them. The filter 230 on the bottom x-ray source 215 is again visible in this view.

Figure 2G:
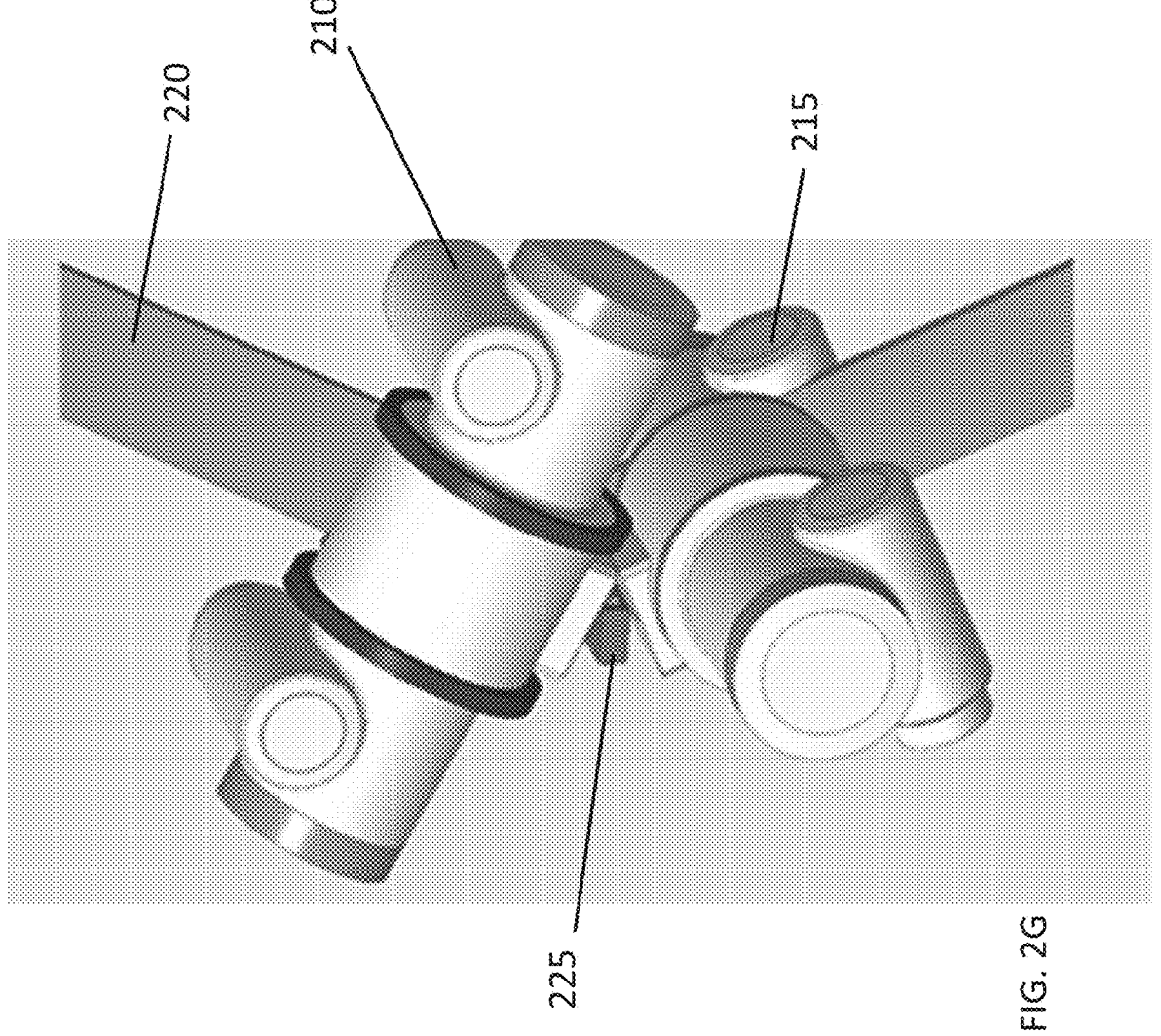
FIG. 2G shows a mode in which the two x-ray sources 210, 215 are mounted to the positioning arms in different orientations.

The x-ray sources 210, 215 can be variously mounted parallel to each other or perpendicular to each other. For example, FIG. 2G shows a mode in which the two x-ray sources 210, 215 are mounted to the positioning arms in different orientations to facilitate FLASH irradiation mode, by allowing the tubes to be positioned closer together. In this example, the vertical structure 220 also rotates the angle of the x-ray sources 210, 215 to allow the tubes to be positioned even more closely to the sample holder 225. In some embodiments, the invention has three or more x-ray sources, which may be mounted on multiple positioning arms at different angles and axes.

Simulation of Parallel-Opposed Geometry

Figure 3B:
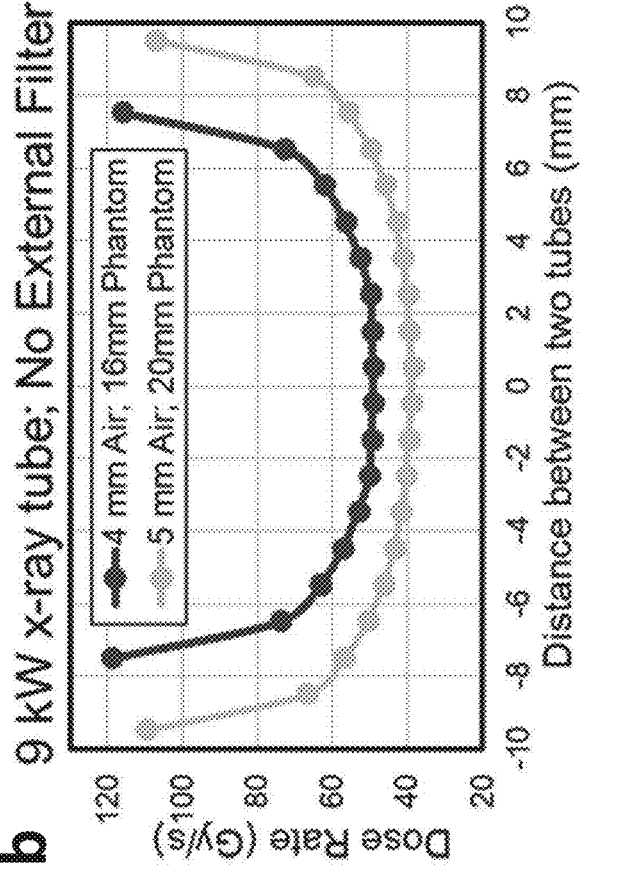
FIG. 3B illustrates the dose rate in water phantom for the setup of FIG. 3A.
Figure 3A:
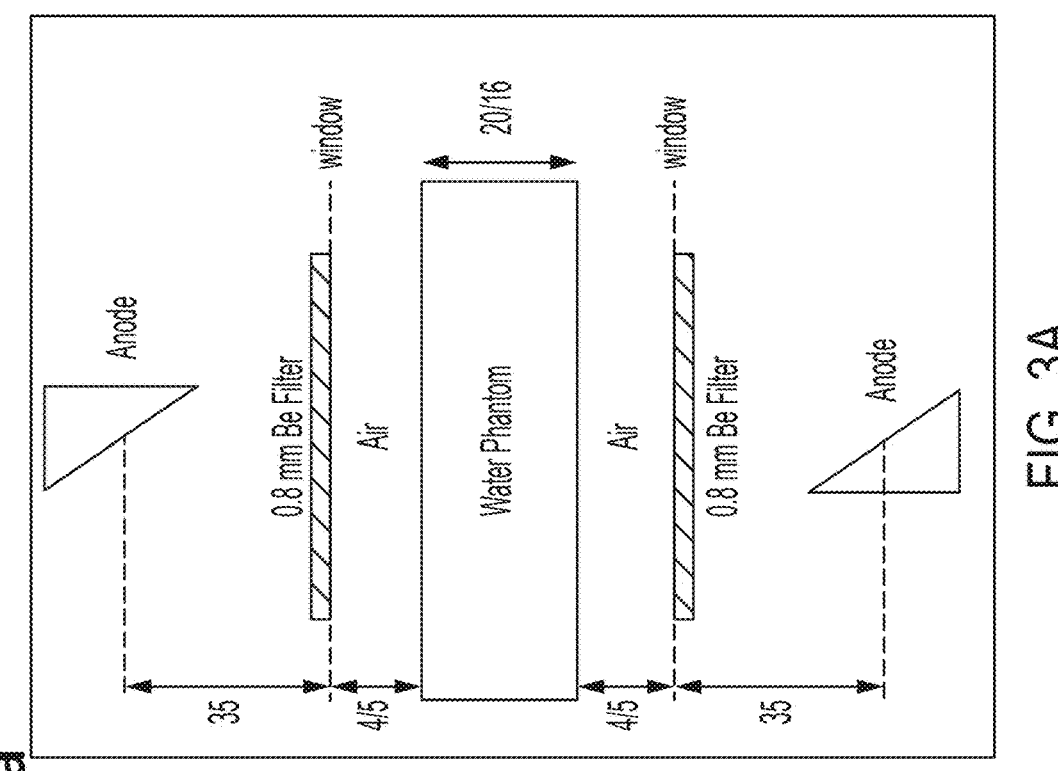
FIG. 3A illustrates a parallel-opposed geometry using two hypothetical 9 kW x-ray sources.

As discussed above, commercially available x-ray cabinet systems using 160 kVp and 165 kVp sources with stationary anodes are not capable of delivering FLASH dose rates at depth. Simulations were conducted to investigate a pair of parallel-opposed x-ray sources, to compensate the rapid drop in depth dose and achieve uniform depth-dose distribution. Anticipating the need of more energetic x-rays and higher beam currents, a Monte Carlo simulation was conducted with a pair of stationary anodes 225 kVp x-ray sources, each powered by a hypothetical 9 kW generator. The 225 kVp source was chosen for shielding consideration. This hypothetical source model would generate x-rays at dose rates higher than 320 kVp x-ray sources with an available maximum 6 kW generator. FIG. 3A shows the system setup under ideal conditions of minimal tube separation and phantom thickness. The schematic illustrates a parallel-opposed geometry using two hypothetical 9 kW x-ray sources. FIG. 3B illustrates the dose rate in water phantom for two different conditions of 4- and 5-mm air with 16- and 20-mm phantom thickness, respectively, with no external filter.

With no external filter, the maximum dose rates are 50 and 40 Gy/s at the center of 16- and 20-mm thick phantoms, respectively. Using minimal filtration (0.01 mm copper) to remove very low keV x-rays, the dose rates reduce to 40 and 32 Gy/s. These outputs only meet the lower end of the suggested FLASH dose rates. The parallel-opposed source arrangement, however, does improve depth dose uniformity over 8-10 mm distance. To achieve dose rates of 100 Gy/s or greater, a high-power generator (>30 kW) and a high-capacity x-ray source would be required, which is not presently available. The conclusion from this simulation was that currently available x-ray sources with stationary anode technology cannot be adapted for FLASH irradiation. X-ray sources with rotating anode technology, however, can be powered to more than 100 kW, and sustain a much higher heat load of 1.2 MJ. Maximum potential of the rotating anode sources is 150 kVp; it is promisingly close to the 165 kVp used in the previous FLASH feasibility study [33].

Simulation of Dosimetric Properties of the X-Ray Source

The RAD-44 tube was modeled in GEANT4 MC Toolkit (CERN, Geneva, Switzerland) to evaluate dosimetric characteristics of its 150 kVp x-ray beam for FLASH and conventional irradiations of a 20-mm thick water phantom. Operational parameters for the RAD-44 tube, and for other tubes by Varex and Canon, are listed in Table 1.

TABLE 1

| Specification | RAD-44 (Varex) | G-1592 (Varex) | E7252X (Canon) |
|---|---|---|---|
| Max Peak Voltage | 150 kV | 150 kV | 150 kV |
| Largest Focal Spot | 2.0 mm | 1.2 mm | 1.2 mm |
| Target Angle | 16° | 12° | 12° |
| Current at Peak Voltage | 600 mA | 600 mA | 600 mA |
| Exposure Time | 0.38 sec | 0.5 sec | 0.3 sec |
| Max. Power | 115 kW | 112 kW | 75 kW |
| Filtration | 0.7 mm Al | 1.0 mm Al | 0.9 mm |
| Distance of Focal Spot to Exit Window | 35 mm | 35 mm | 35 mm |
| Anode Heat Capacity | 0.3 MJ | 1.1 MJ | 0.21 MJ |

FLASH Irradiation

Figure 4A:
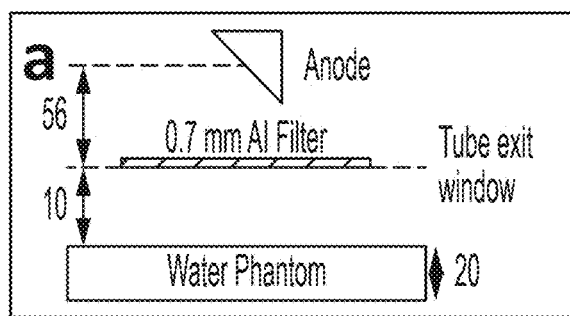
FIGS. 4A and 4B show schematics of experimental setups for FLASH irradiation.
Figure 4B:
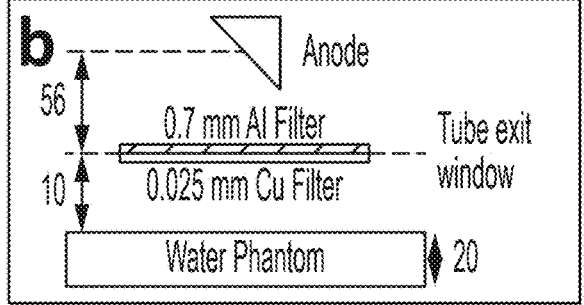
Figure 4C:
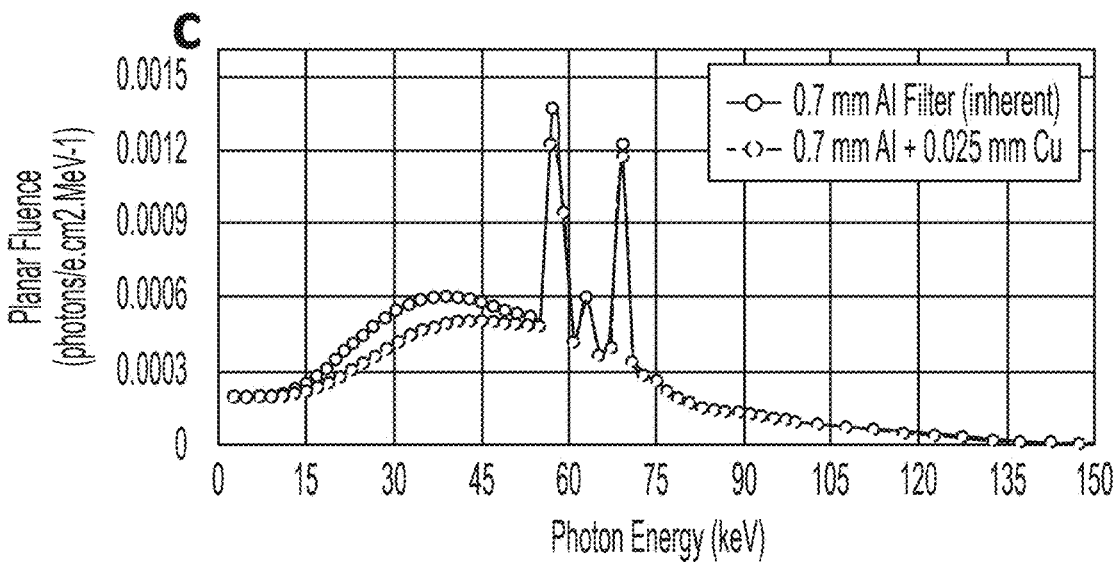
FIGS. 4C and 4D shows the energy spectrum and depth dose-rate curve for the experimental setups in FIGS. 4A and 4B.
Figure 4D:
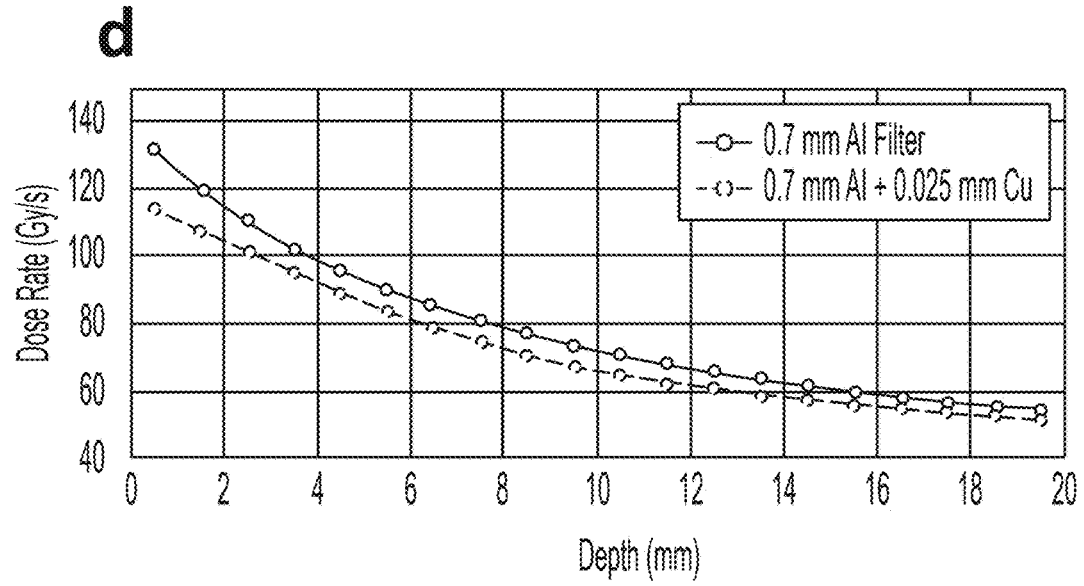

Phase-space energy spectra for the x-ray beam were calculated at different distances from the tube exit window. FIGS. 4A and 4B show schematics of system setup with the phantom located at 10 mm distance from the tube. FIG. 4C shows the energy spectrum of a 150 kVp x-ray beam from 4×4 mm area at the central beam axis at the phantom surface from the RAD-44 tube. FIG. 4D illustrates the depth dose-rate curve in the water phantom. Dimensions are in mm.

The inherent Al filter efficiently absorbs photons with energies less than 15 keV and Cu filter further reduces photon fluence below 45 keV. This filtration hardens the beam to reduce high surface dose contribution and produces a beam with relatively uniform low-LET (see FIG. 14 below). As shown in FIG. 4D, the 150 kVp x-ray beam generated at 800 mA tube current can produce the dose rates of 132 and 71.5 Gy/s at the phantom surface and center, respectively. Addition of Cu filter slightly reduces the dose rates, particularly at shallow depth of the phantom.

FIG. 5A shows a schematic of parallel-opposed setup with mirrored beams to offset the heel effect, and the corresponding depth dose-rate curve in the water phantom. FIGS. 5B and 5C show an MC simulation of depth dose-rate curve in the phantom from 150 kVp x-ray beam generated by the RAD-44 tubes at 800 mA current. Additional technique parameters are voltage 150 kV, current 600 mA, exposure time 0.38 s, focal spot 2.0 mm, anode angle 16 deg., inherent filter 0.7 mm Al, and distance of focal spot to exit window of 35 mm.

At 10 mm distance between tubes and phantom surfaces, dose rate at the phantom center is 140.5 Gy/s. It reduces to 127.4 Gy/s by 0.025 mm Cu added filtration. A uniform depth-dose rate within 5% deviation is achieved over 8-10 mm in the central region of the phantom.

FIGS. 6A-6C show cross-beam dose-rate distributions in the central slice of the phantom from single and opposing pair of the x-ray sources using the external Cu filter. Specifically, FIGS. 6A-6C show the dose rate distribution at the central slice of a 20-mm thick water phantom located at 10 mm distance from (FIG. 6A) single beam, (FIG. 6B) parallel-opposed beams with 0.025 mm Cu filter, and (FIG. 6C) corresponding in-line and cross-line dose-rate profiles from the distributions. In-line is parallel to cathode-anode direction of x-ray source.

The heel effect is clearly observed in the dose-rate distribution from single x-ray tube. On the other hand, parallel-opposed mirrored sources minimize heel effect, resulting in a relatively uniform dose-rate distribution. Flatness and symmetry of ±3% is achieved in the central region of the 20 mm×30 mm field. FIG. 6C also shows a sharp, less than 1 mm wide, beam penumbra, as expected from the 16-degree anode angle, 2 mm focal spot, and the irradiation geometry of FIG. 5A. The small penumbra accentuates the advantage of kV x-ray beam over high energy electron and proton beams for small animal research.

Figures 7A, 7B, 7C, 7D, 7E:
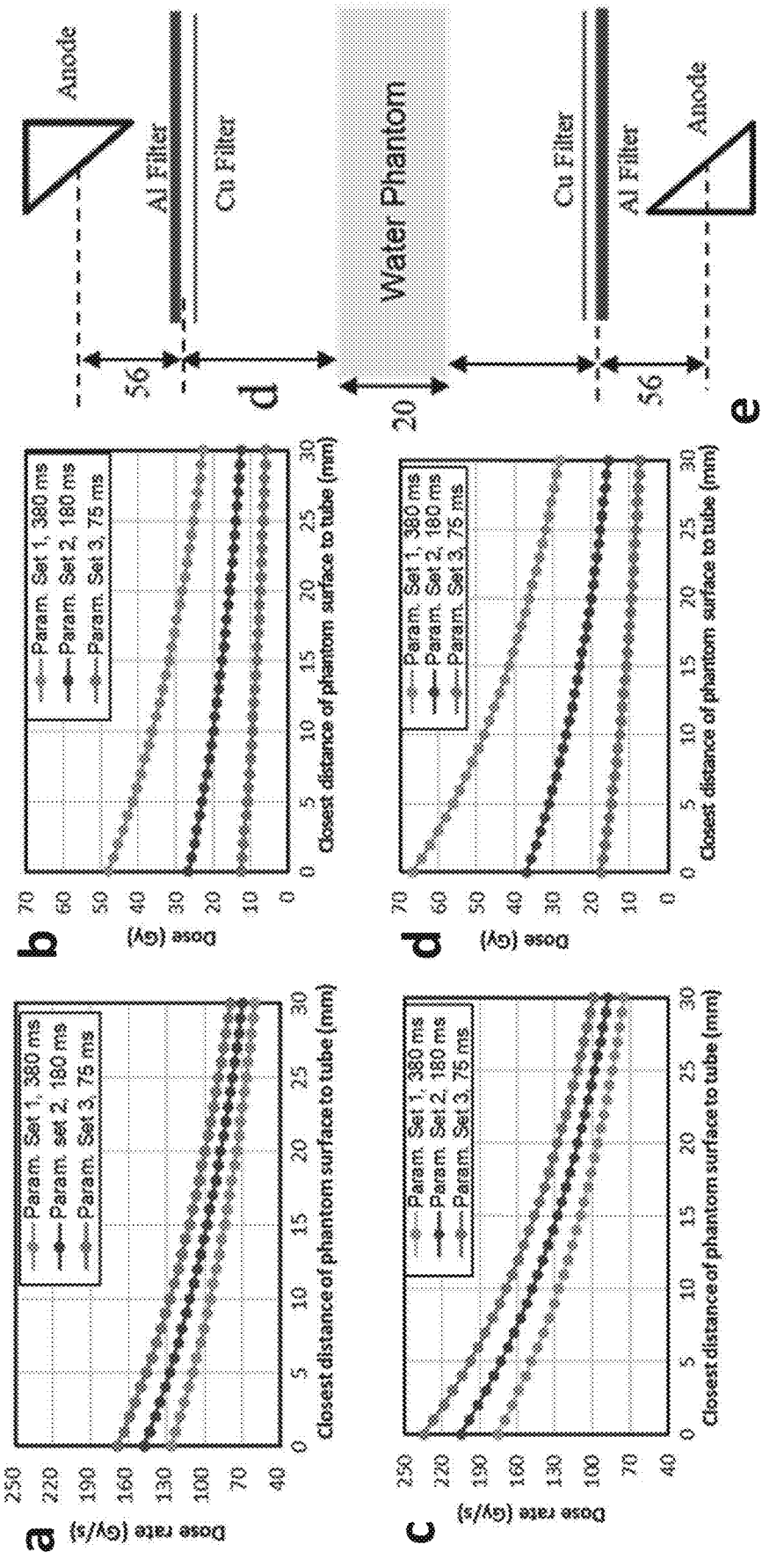
FIGS. 7A-7D show single-pulse FLASH dose rate and dose as a function of the distance between a 20-mm thick water phantom surface and the x-ray tubes in a parallel-opposed geometry.
FIG. 7E illustrates the experimental setup for the simulation in FIGS. 7A-7D.

For the parallel-opposed beams with Cu filter, FIGS. 7A-7D show FLASH dose rates and doses in the center and surface of the water phantom as a function of distance between phantom surface and the tubes for three different exposure times and tube currents. Parameter set 1 is 600 mA, set 2 is 700 mA, and set 3 is 800 mA. FIG. 7A shows dose rates and FIG. 7B shows doses at phantom center, and FIG. 7C shows dose rates and FIG. 7D shows doses at phantom surface. FIG. 7E illustrates the experimental setup for the simulation. Phantom center emulates internal tissues of small animals such as lung and intestine, and phantom surface depicts superficial tissues such as skin. The exposure times are 75, 180, and 380 ms for currents of 800, 700, and 600 mA, respectively, to show the balance in the delivery of dose rate and absolute dose using the rotating anode technology. FIGS. 7A-7D also show that FLASH dose rate and dose reduce with distance between the phantom and tubes due to the inverse square effect.

Maximum dose rates of 234.6 and 168.9 Gy/s can be achieved at the surface and center of the phantom, respectively, by attaching the tubes to the phantom (i.e. zero distance). At 5 mm distance from the tube (i.e. allowing for workspace), the corresponding dose rates are 204.3 and 150.1 Gy/s. At these dose rates, a single 75 ms pulse of x-ray beam can deliver 15.0 and 11.3 Gy doses to the phantom surface and center, respectively. Larger doses up to 67 Gy can be delivered at longer exposure times with lower FLASH dose rates. For example, at 5 mm distance, 52.3 and 42.8 Gy can be delivered at the dose rates of 153.2 and 112.6 Gy/s to the phantom surface and center, respectively, in a single x-ray pulse of 380 ms. FIGS. 7A-7D collectively show the relationship of dose output and workspace (i.e. tube separation) in accommodating FLASH studies using the proposed system. Higher dose rates and doses can be delivered than those shown in FIGS. 7A-7D for samples less than 20 mm thick. The flexible range of dose rates and doses will be advantageous to elucidate their relationship with FLASH effect.

Conventional Irradiation

Figures 8A, 8B, 8C:
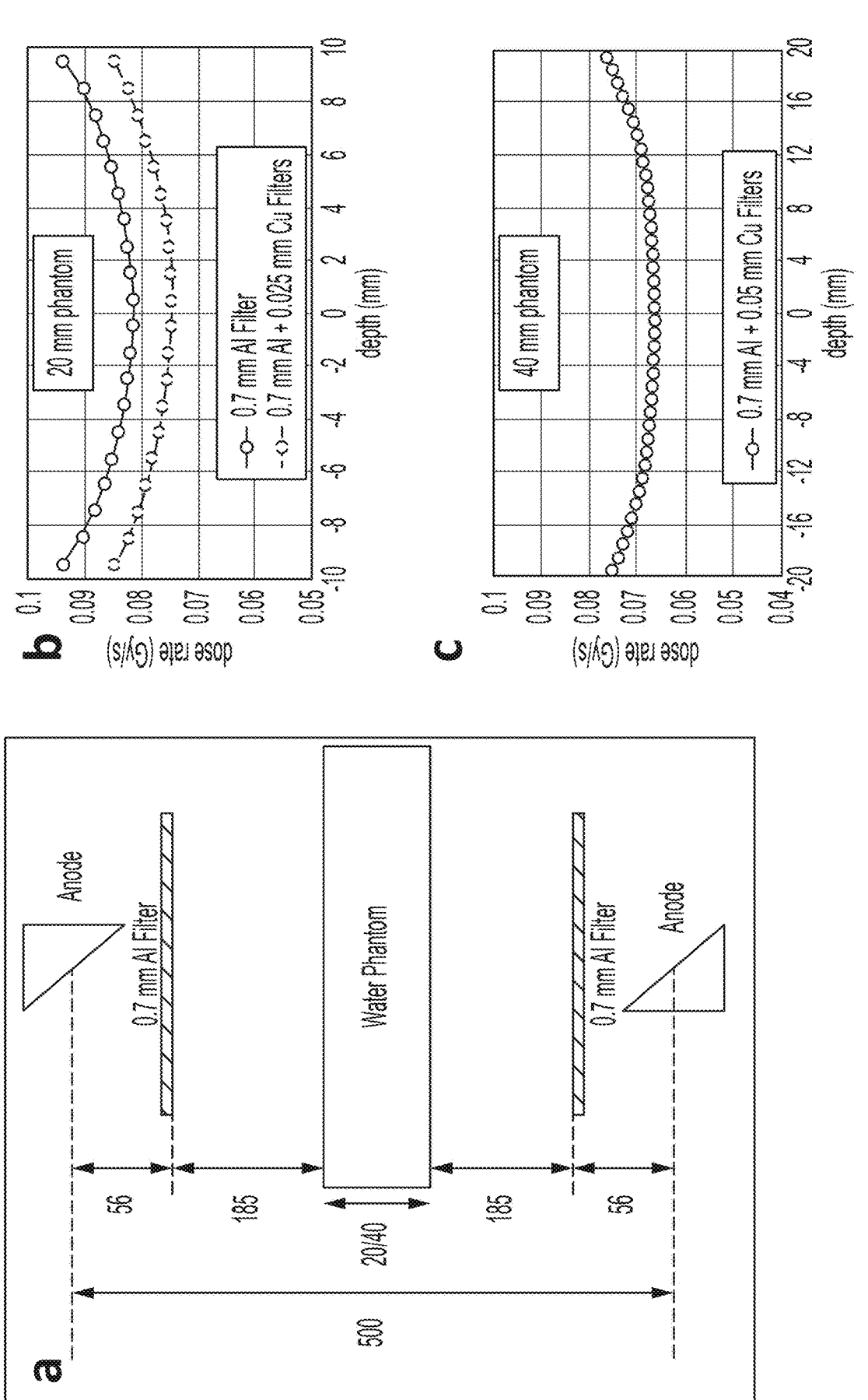
FIGS. 8A-8C show a schematic of conventional irradiation setup, with depth dose-rate curves in a 20-mm and a 40-mm thick water phantom.

In some embodiments, the proposed system is capable of conventional dose rate irradiation (≤0.1 Gy/s), designed to support comparative studies with FLASH irradiation. This is achieved by increasing the distance between phantom and the tubes, and reducing the tube current. FIG. 8A illustrates a schematic of a conventional irradiation setup, of parallel-opposed x-ray sources at the distance of 185 mm from a 20-mm and 40-mm thick water phantom, and FIG. 8B shows depth dose-rate curves in the phantoms at tube current of 5 mA used for the simulation. For the 20-mm thick phantom, dose rates at the center of the phantom are 0.081 and 0.075 Gy/s for the beam filtration of inherent Al and external Cu, respectively. As expected, the depth-dose uniformity is improved compared to FLASH, because of reduced inverse square effect. FIG. 8C shows a relatively uniform (within 5%) depth dose-rate in a 40-mm thick water phantom over a 27-mm thickness in central region of the phantom. Thus, the proposed parallel-opposed x-ray sources system provides added flexibility as a preclinical irradiator by accommodating thicker medium at conventional dose rates.

Field Dimension

The RAD-44 x-ray source provides field dimensions well suitable for small animal irradiation. Table 2 summarizes Field size, FLASH, and conventional dose rates in a 20 mm thick water phantom as a function of the distance between tubes and the phantom surface from parallel-opposed RAD-44 sources. Flatness and symmetry can be refined by energy filters. For FLASH irradiation, even the smallest field size of 38 mm×19 mm achieved at zero distance can accommodate irradiation of most small animal tissues and organs. At larger distances, it is feasible to achieve lower FLASH dose rates of 40-100 Gy/s for field sizes greater than 61 mm×30 mm.

TABLE 2

| Closest distance of phantom surface from tube (mm) | Field size (mm) at phantom center | FLASH dose rate (Gy/s) at phantom center/surface | Conv. Dose Rate (Gy/s) at phantom center |
|---|---|---|---|
| 0 | 38 × 19 | 169/235 | NA |
| 5 | 41 × 20 | 146/198 | NA |
| 10 | 44 × 22 | 127/169 | NA |
| 20 | 52 × 26 | 99/127 | NA |
| 30 | 61 × 30 | 80/99 | 0.50 |
| 185 | 105 × 53 | NA | 0.075 |
| 200 | 115 × 57 | NA | 0.07 |
| 250 | 143 × 72 | NA | 0.05 |

Beam Angle

Preclinical irradiators with single kV x-ray source deliver depth dose with steep gradient. In the parallel-opposed geometry, both entrance and exit doses can remain higher than dose at depth, especially for short separation distances between x-ray sources. Our results in FIG. 5C show 25-30% higher entrance and exit doses than the dose at the phantom center. The high doses may not be a concern for FLASH irradiation since FLASH effects are suggested to reduce normal tissue toxicity to radiation. For completeness, nevertheless, a dosimetric solution of beam angling is devised to minimize the high entrance and exit doses.

Figure 9F:
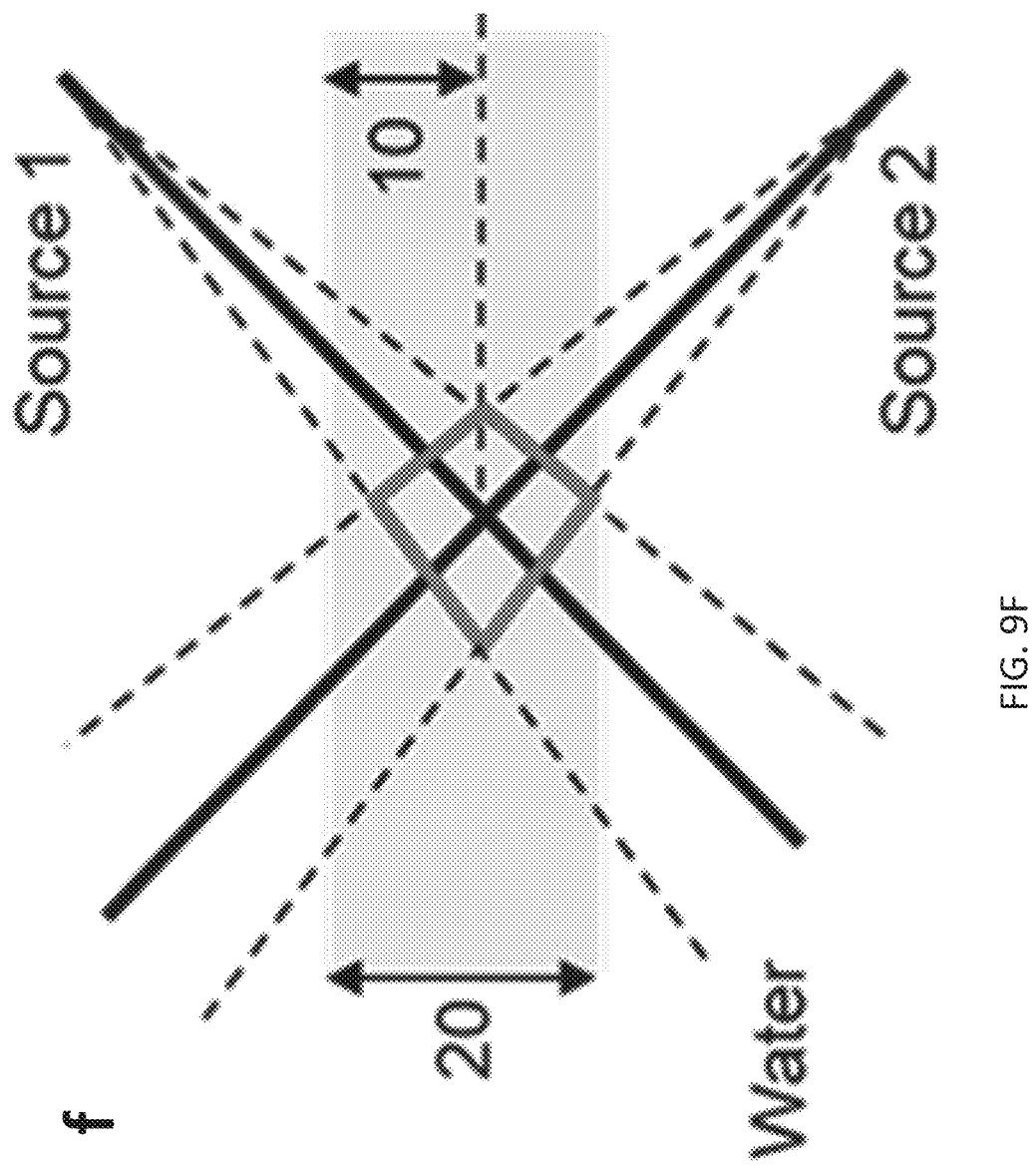

FIG. 9A shows a schematic of beam angling to avoid or minimize beam overlap, and thereby minimize high entrance and exit doses, at the entrance and exit surfaces. As an example, the dose-rate distribution was simulated in a 20-mm thick water phantom irradiated by 10 mm×10 mm fields at the beam angle of 26 degrees from the vertical for each of two x-ray sources 910, 915. FIGS. 9B-9E show the dose-rate distribution at the phantom center (10 mm depth), intermediate depths (3- and 5-mm depth), and the surface. Arrows indicate different possible source positions. The dose-rate distributions are shown at the center (FIG. 9B), surface (FIG. 9C), 5 mm depth (FIG. 9D), and 3 mm depth (FIG. 9E) of the phantom from a pair of beams of 10 mm×10 mm and 26 degrees from vertical. The beams do not overlap at the phantom surfaces, but fully intercept at the phantom center. FIG. 9F shows a diagram of the irradiation volume defined by the intersection of the beams.

Figures 10A, 10B, 10C:
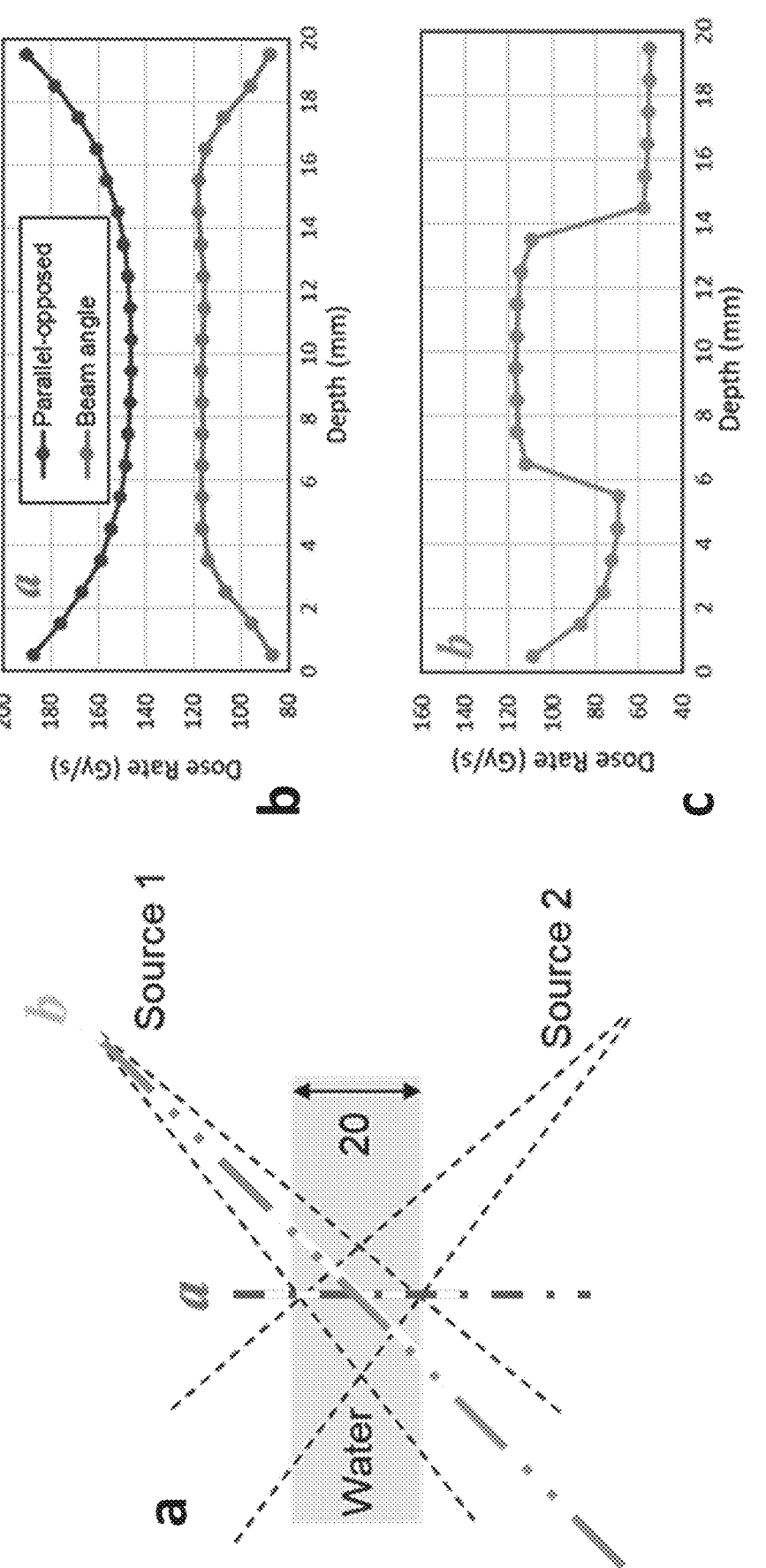
FIGS. 10A-10C illustrate a schematic of beam angling for irradiating a 20-mm thick water phantom.

FIGS. 10A-10C illustrate a schematic of beam angling for irradiating a 20-mm thick water phantom.

FIG. 10A shows two profiles of the dose distribution, along lines A and B to indicate the direction of dose profile. Profile A runs along the vertical depth of the phantom, and profile B runs along the axis of beam 1 inside the phantom. Profiles A are shown in FIG. 10B for parallel-opposed (upper curve) and rotated (lower curve) sources with a 26-degree beam angle. In FIG. 10C, profile B is for rotated source 1.

Profile A (dot-dashed line) shows 25% decrease in the entrance and exit doses in comparison with the dose at the phantom center. Profile B (double-dot-dashed line) shows the characteristics attenuation of beam 1 except for the overlapping region of the two beams. The maximum entrance dose in profile B is 7% lower than the dose at center. Beam angling of the paired x-ray sources, however, reduces dose rate, as shown in FIG. 10B, to 20% less in the phantom center than for parallel-opposed sources. The beam penumbra is also broadened. It is noteworthy that, in addition to reducing high surface doses, beam angling provides a first order capability of conformal irradiation for the parallel-opposed beam arrangement. Direct impingement of a critical structure can be avoided at the expenses of dose distribution quality. It follows then that 3D treatment planning utilities for some embodiments of the system, such as dose volume histogram, will be of great value to facilitate conformal irradiation and the evaluation of dosimetric quality.

Measurement of Dosimetric Properties of the X-Ray Source System Design

Some embodiments of the self-shielded cabinet system include stands to mount two x-ray sources, computerized control systems for sources motion, docking system with mouse bed, sets of collimator and filter, and cameras. The cabinet system is portable in some embodiments, equipped with wheels for ease of transport and installation at appropriate laboratory locations.

Mechanical Movement of X-Ray Sources

The cabinet is equipped in some embodiments with computer-controlled robotic system for translation and rotation of x-ray sources to accurately and reproducibly position them with respect to radiation isocenter. In some embodiments, the system provides the X-ray tubes with independent bidirectional computer-controlled vertical motion up to 250 mm with 0.5 mm accuracy to support fine adjustment of SSD. Each tube also has in some embodiments independent unidirectional rotational motion in the range of 0-25 degree from vertical axis with 0.2-degree accuracy to support beam angling for conformal and angled irradiation.

Figure 11A:
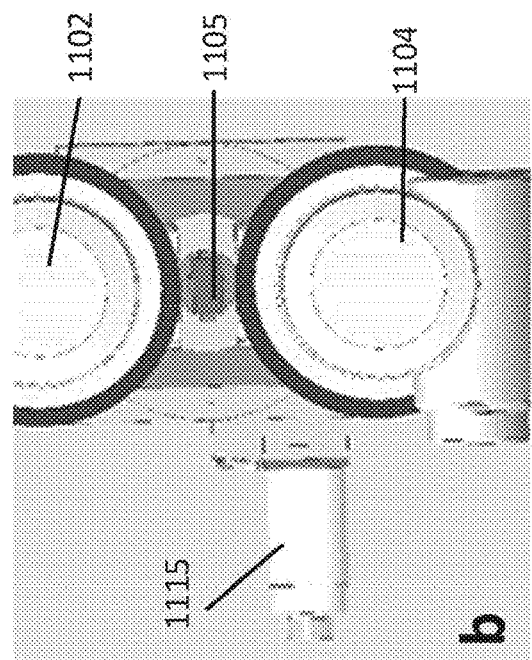
FIGS. 11A-11C illustrate schematics of a two system design for FLASH irradiation including parallel-opposed and rotated x-ray source configurations.
Figure 11B:
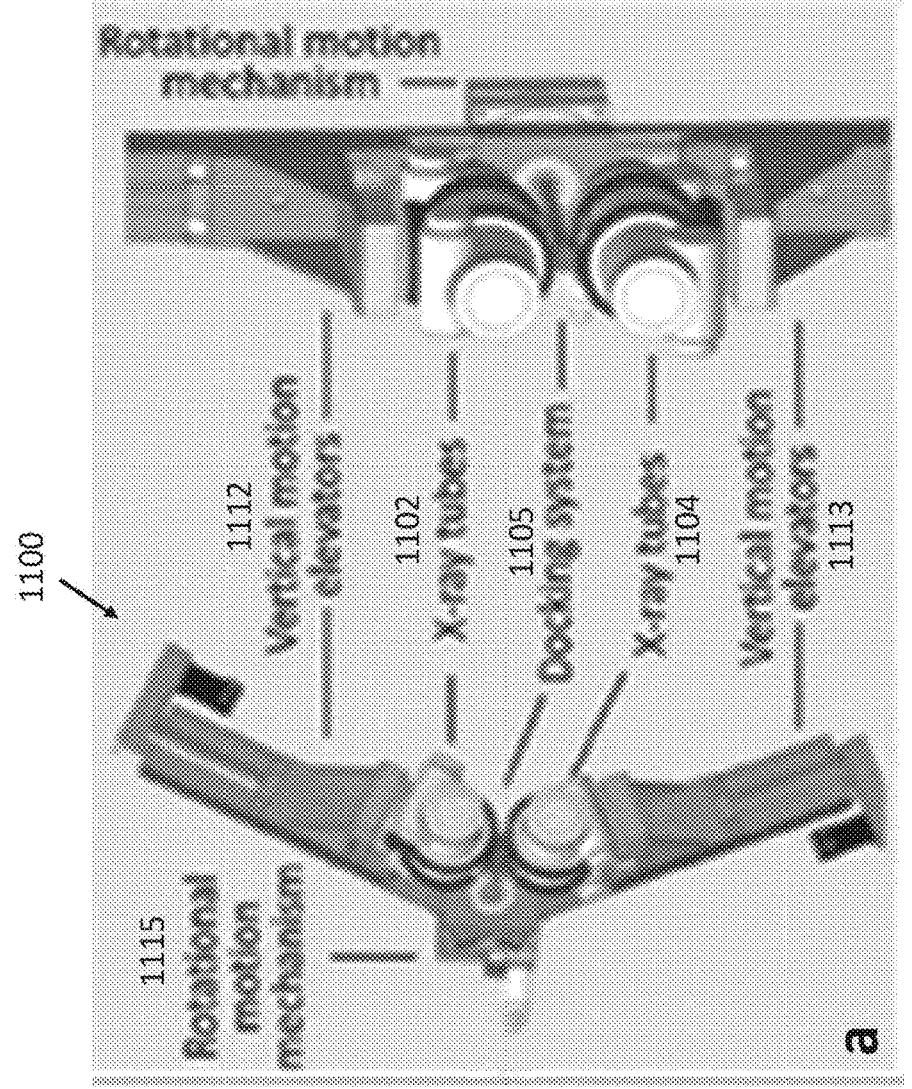
Figure 11C:
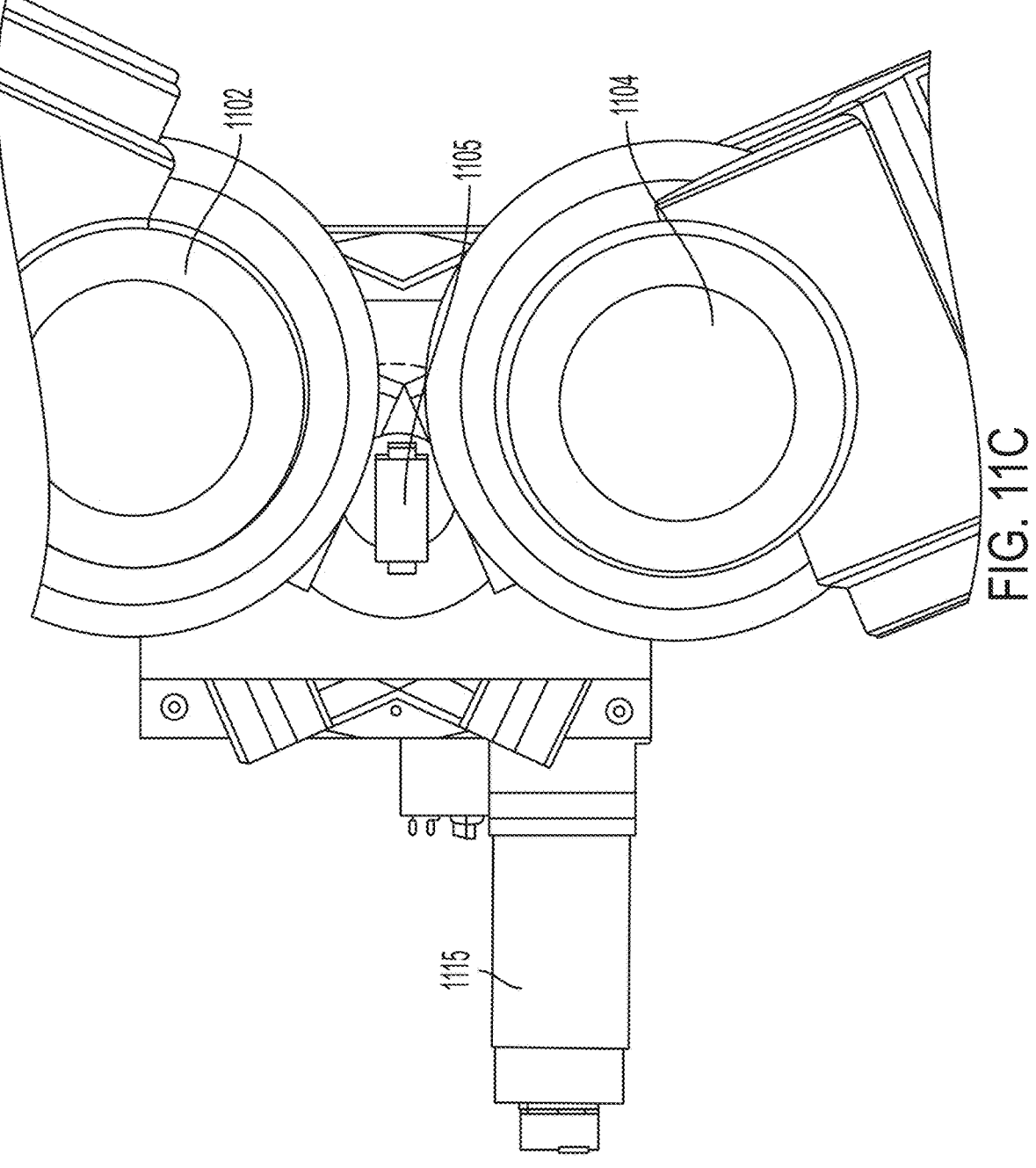

FIGS. 11A-11C shows schematics of a two-system design 1100 for FLASH irradiation in some embodiments, including parallel-opposed (right) and rotated (left) x-ray source configurations, where the x-ray tubes 1102, 1104 are in close proximity to a sample. In FIG. 11A, a docking system 1105, a computer-controlled vertical motion systems 1112, 1113 and rotational motion system 1115, are also shown. FIG. 11B shows a close-up of the parallel-opposed setup. FIG. 11C shows a close-up of the orthogonally rotated setup, where one tube 1102 is rotated clockwise and the other tube 1104 rotated counterclockwise to avoid beam overlap while bringing them closer towards each other. At distances shorter than 10 mm between the tubes 1102, 1104 and the sample, the rotation of both tubes will be limited to smaller angles (10°-20°, this range looks big for such small separations) due to collision of the tubes housing.

Docking System for a Mouse Subject

Given the confines of the proposed system, a multi-purpose docking system is required in some embodiments to facilitate accurate and reproducible positioning of a mouse subject for irradiation. Some embodiments of the docking system include a mouse bed, subject alignment utilities, immobilization, positioning verification, gas anesthesia support, and temperature control of the animal. Several types of multi-purpose docking system for preclinical irradiators have been developed in some embodiments, such as SARRP and imaging systems (e.g., mouse cone-beam CT (CBCT) and MuriGlo).

Figure 12:
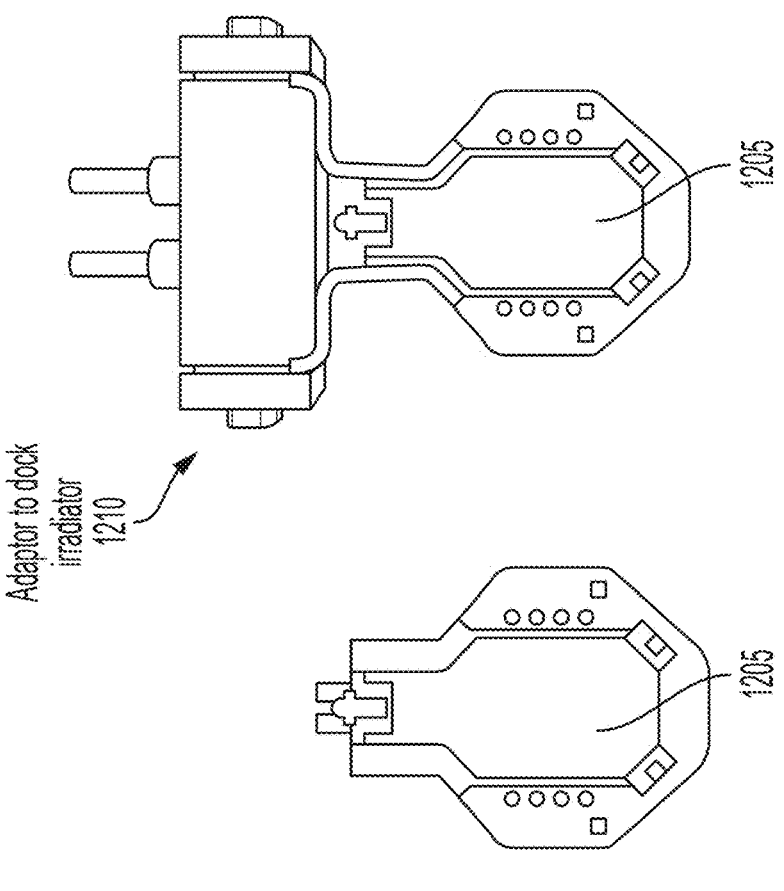
FIG. 12 illustrates a flexible mouse bed with its adaptor of some embodiments.
Figure 12:
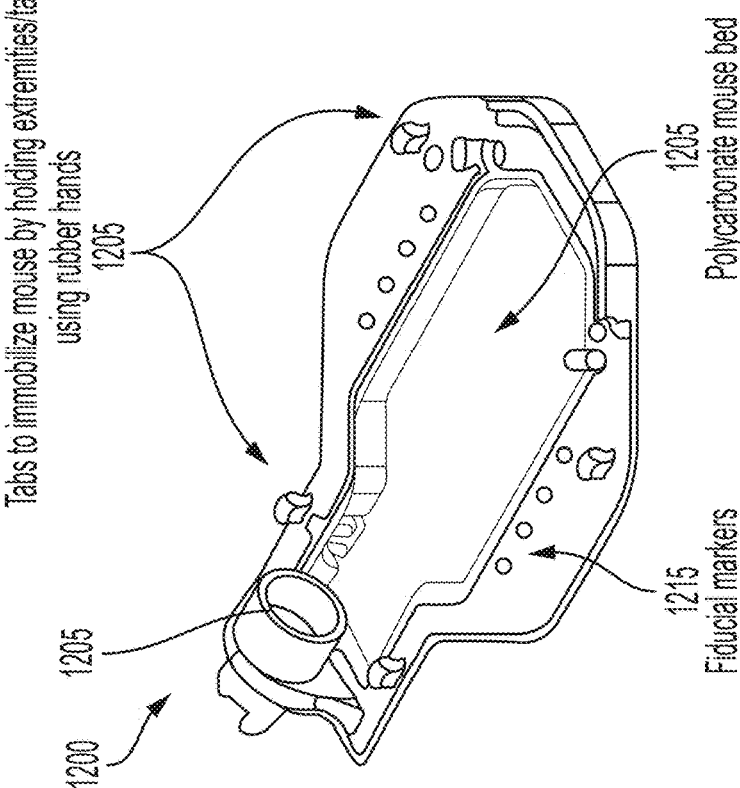

FIG. 12 illustrates a docking system 1200 with a flexible mouse bed 1205 and its adaptor 1210 of some embodiments. It includes a polycarbonate mouse bed 1205, fiducial markers 1215 for positioning, immobilization tabs 1220 for holding the mouse during the irradiation procedure, and a nose holder 1225 for flowing anesthesia gas. The adaptor 1210 connects the mouse bed 1205 to the irradiator at the isocenter level and allows the mouse to receive anesthetic gas during positioning and irradiation. The mouse bed 1205 also incorporates a temperature control system in some embodiments, to prevent mouse hypothermia during the irradiation procedure. Given the unidirectional gantry rotation in our proposed system, two different beds are developed in different embodiments for head and feet first-in positions. A mouse is placed in either of the beds depending on irradiation site, its position is adjusted based on off-line CBCT images and the bed fiducials, and then docked to the system for irradiation. The mouse bed 1205 is also designed in some embodiments to hold Gafchromic quality assurance films for the mouse position verification. Film (or thin imaging plate such as used for dental radiography) is a preferred imaging medium for verification over an on-board flat panel imager, as the space between the mouse and x-ray tubes is limited in some embodiments for FLASH irradiation. The cabinet is also equipped in some embodiments with a system of lasers and optical cameras to facilitate accurate and reproducible sample alignment setup and monitoring.

Flat Panel Imager

Some embodiments employ a high resolution, CMOS flat panel imager (C7942CA-22, Hamamatsu Corp.) for quality assurance tasks and verification of the designed system setup and alignment.

Collimators and Energy Filters

FLASH and conventional collimator sets are designed and fabricated in some embodiments to provide multiple field sizes pertinent to the deliverable field dimensions of the RAD-44 (see Table 2) and typical irradiation fields for mouse models. Each standard set of fixed rectangular and square openings is made of 1.0 mm thick tungsten in some embodiments. At this thickness, the transmissions of 100 and 150 keV x-ray photons are 0.00010% and 0.04% of the incident beam, respectively. As needed, other custom-shaped collimators are fabricated in some embodiments from different materials, such as brass, that are thicker but more amenable to machining compared with tungsten. Energy filters are designed in some embodiments, particularly for angled source positions, to provide beams with desirable flatness and symmetry in water phantoms with the thicknesses up to 20 mm. The external filters are predominantly metallic, e.g. made from cut copper sheets or 3D printed. The collimator and filter assembly are docked in some embodiments to the output port of the RAD-44 tube housing. A hollow spacing of 4-18 mm inside the port is allowed in some embodiments for secured docking of the collimator and filter assembly.

Cabinet Frame and Shielding

The cabinet frame is designed based on the shielding requirement and assembly of the system components inside the cabinet for optimal operation. The cabinet is adequately shielded for radiation in adherence to regulatory requirements for safe operation. The shielding thickness is expected to be less than that of the SARRP, in some embodiments.

Monte Carlo (MC) Based Dose Calculation System

A MC dose engine is an essential subsystem for the FLASH cabinet system in some embodiments. Given the suggested sensitivity of FLASH effect to LET, MC has capability to calculate LET distribution in the irradiated samples and provides a useful tool for the study of LET effect in FLASH. In addition, MC creates a platform for further research on biophysical and biological models for both FLASH and conventional irradiations.

The MC dose engine of some embodiments is based on GEANT4, a general object-oriented track structure toolkit [42]. GEANT4 has all necessary physics and simulation utilities required for the project. In particular, it has three physics models for low energy radiation (Livermore, Penelope, and G4EmDNA), which are applicable to the kV x-ray sources used for clinical and preclinical dose calculation [43,44]. The MC dose engine is connected in some embodiments to the MuriPlan 3D treatment planning system (Xstrahl, Suwanee G A) to provide visualization of dose distribution on phantom and mouse anatomy.

Validation

MC simulations are validated in some embodiments by comparing calculated dosimetric parameters with measurements using the RAD-44 x-ray source. Preliminary results using GEANT4 to model the RAD-44 are shown above in the discussion of dosimetric simulations. For validation of the initial simulations, a fluoroscopy tube (Varex RAD-94; 140 kVp, 0.5 mm Al filter) was used to approximate the RAD-44. Exposures in a solid water phantom using the RAD-94 were measured with radiochromic films and compared with the RAD-44 simulations, with the following additional parameters: Filtration: 0.5 mm Al (measured) versus 0.7 mm Al (calculated). Tube voltage: 140 kVp (measured) versus 150 kVp (calculated). Other parameters: 66.0 mm SSD, 140 kV, 200 mA, 0.30 s.

Figure 13:
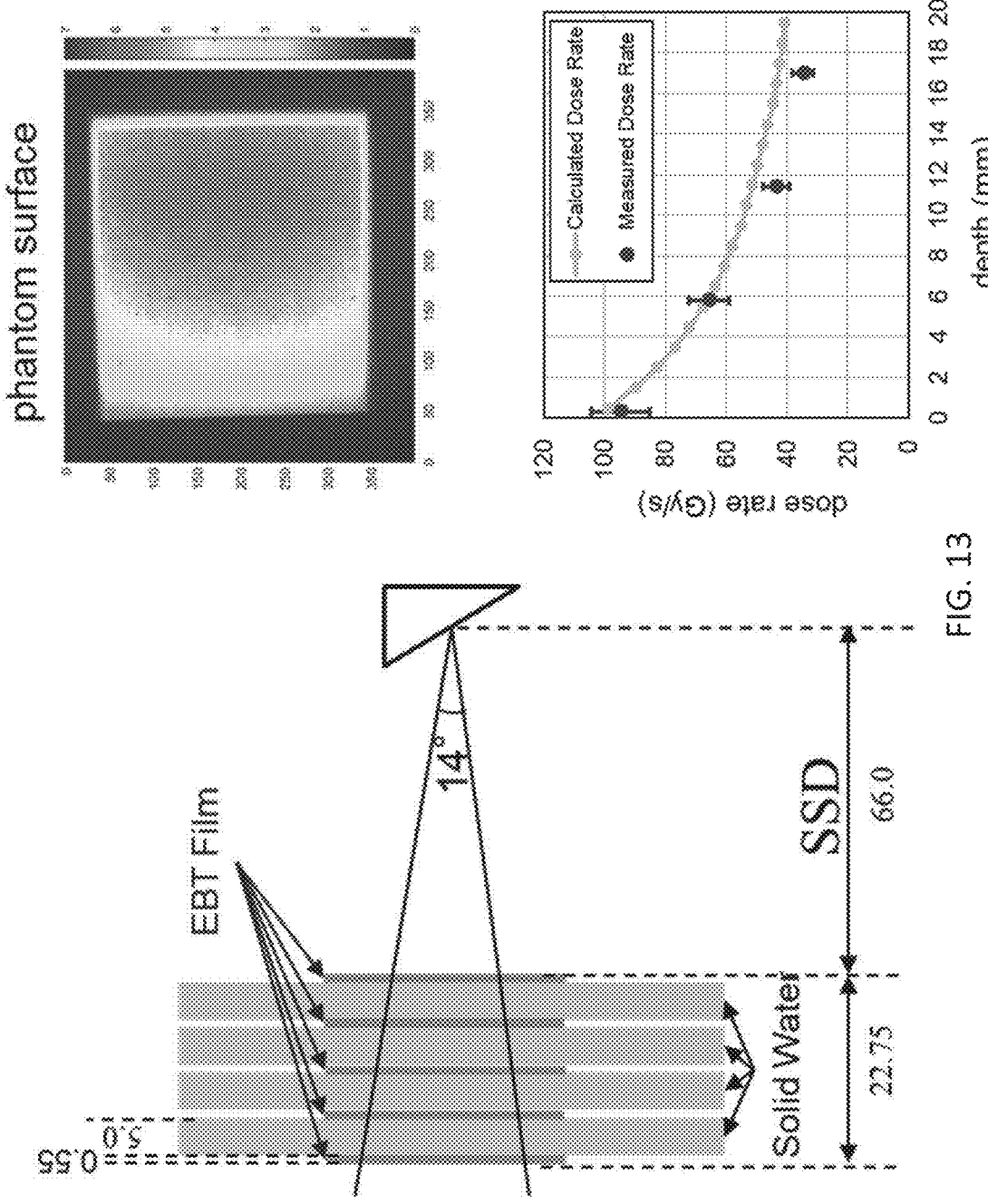
FIG. 13 shows calculated and measured depth dose-rate curve for FLASH irradiation using the RAD-44 (calculated) and the RAD-94 (measured) x-ray sources.

FIG. 13 shows the results of depth dose-rate for both measurement and simulation. Excellent agreements were achieved at shallow depths of the phantom (<10 mm). Deviations at deeper depths were expected, due to the softer beam of the RAD-94 compared to that of the RAD-44 (150 kVp and 0.7 mm Al filter). The comparison provides confidence in simulations on using the RAD-44 for FLASH irradiation.

Dose Calculation 3D dose calculation and distribution with high resolution matrices are also developed in some embodiments. The models and simulations for higher resolution and more accurate dosimetry are improved in some embodiments using a high capacity 18 cores GPU workstation. To increase speed and accuracy of the dose calculation, high resolution phase-space energy spectra are generated in some embodiments for various external filters and collimators designed for the FLASH and conventional irradiations. The GEANT4 dose engine uses the precomputed phase space files to calculate the dose and LET in 3D matrices. MC dose calculations are conducted in some embodiments for (1) phantoms based on known material compositions and (2) heterogeneous mouse subjects based on CBCT images.

Dosimetric parameters include, and are not limited to, dose, dose rate, beam quality, field size, penumbra, depth uniformity, flatness, and symmetry. These are quantified as a function of medium thickness, SSD, gantry angulation, collimator and energy filters in some embodiments. In addition, several important parameters of x-ray source such as exposure time are also validated in some embodiments. The precision and accuracy of the dosimetric measurements is expected to be within 5% of calculations in some embodiments, quantified for continuing quality assurance purposes.

LET Calculation

Knowledge of LET distributions in an irradiated medium is important in understanding FLASH effects. GEANT4 is able to simulate track structures and the interaction processes of electrons in 0.1-1000 keV kinetic energy range using the low-energy radiation physics models such as Livermore [43]. It is thus feasible to simulate LET distribution using GEANT4 in any irradiated medium. From the dose and LET calculations, it is also feasible to estimate the distributions of the reactive chemical radical species produced by the radiation ionization events. The radical distributions provide the link of the released radiation energy to the observed biological damages due to FLASH irradiation.

Figure 14:
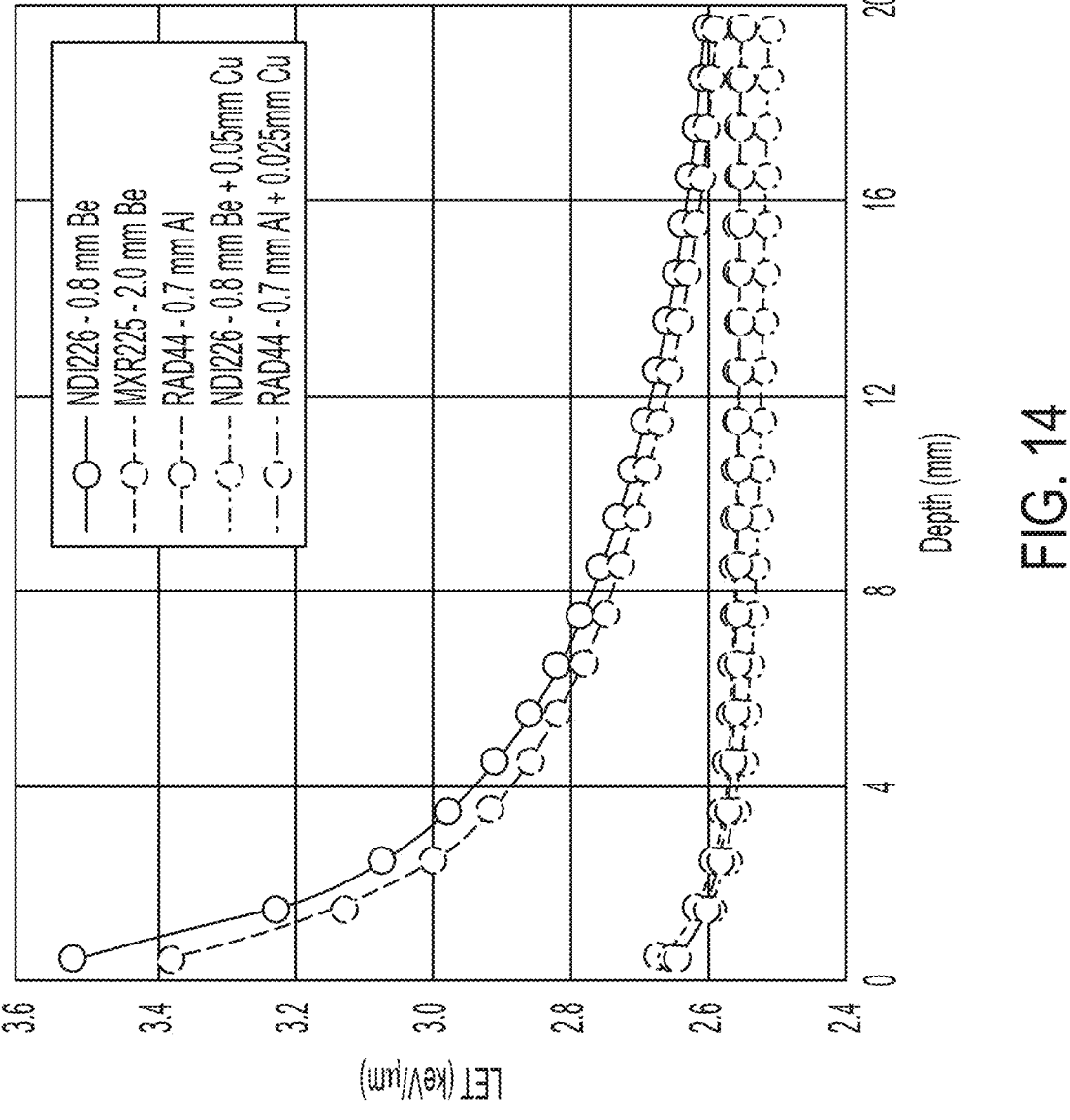
FIG. 14 compares depth LET curves for the RAD-44 and two stationary anode x-ray sources at different filtrations.

FIG. 14 compares depth LET curves for the RAD-44 and two stationary anode x-ray sources at different filtrations. Minimum filtration such as 0.8 mm Beryllium (Be) produces a non-uniform LET distribution with depth. Adding external Al or Cu filters improves the uniformity of LET, particularly at deeper depths of the water phantom. Besides x-ray beams, the MC-based LET calculation can be utilized as a general tool in FLASH effect research using radiations with different LET.

REFERENCES

1. Montay-Gruel P, et al (2019). Long-term neurocognitive benefits of FLASH radiotherapy by reduced reactive oxygen species. Proc. Natl. Acad. Sci. U.S.A. 116(22): 10943-10951.
2. Vozenin M C, et al (2019). The advantage of FLASH radiotherapy confirmed in mini-pig and cat-cancer patients. Clin. Cancer Res. 25(1): 35-42.
3. Wilson J D, Hammond E M, Higgins G S, Petersson K (2020). Ultra-high dose rate (FLASH) radiotherapy: Silver bullet or fool's gold? Front. Oncol. 9:1563.
4. Montay-Gruel P, et al (2018). X-ray can trigger the FLASH effect: Ultra-high dose-rate synchrotron light source prevents normal brain injury after whole brain irradiation in mice. Radiother, Oncol, 129: 582-588.
5. Workshop on Ion Beam Therapy (2013), Office of Science, U.S. Dep. of Energy. https://science.osti.gov/-/media/hep/pdf/accelerator-rd-stewardship/Workshop_on_Ion_Beam_Therapy_Report_Final_R1.pdf
6. Loo B W, et al (2014). Pluridirectional very high electron energy radiation therapy systems and processes. Patent no. US 2014/0135563.
7. Vozenin M C, Hendry J H, Limoli C L (2019). Biological benefits of ultra-high dose rate FLASH radiotherapy: sleeping beauty awoken. Clin. Oncol. 31:407-15.
8. Favaudon V, Caplier L, Monceau V, Pouzoulet F, SayarathM, Fouillade C, et al (2014). Ultrahigh dose-rate FLASH irradiation increases the differential response between normal and tumor tissue in mice. Sci. Transl. Med. 6:245ra93.
9. Fouillade C, Curras-Alonso S, Giuranno L, Quelennec E, Heinrich S, Bonnet-Boissinot S, et al (2020). FLASH irradiation spares lung progenitor cells and limits the incidence of radio-induced senescence. Clin. Cancer Res. 26:1497-506.
10. Girdhani S, Abel E, Katsis A, Rodriquez A, Senapati S, KuVillanueva A, et al (2019). FLASH: A novel paradigm changing tumor irradiation platform that enhances therapeutic ratio by reducing normal tissue toxicity and activating immune pathways. Cancer Res. (2019) 79(13 Suppl):LB-280.
11. Diffenderfer E S, et al (2020). Design, implementation, and in vivo validation of a novel proton FLASH radiation therapy system. Int. J. Rad. Onc. Biol. Phys. 106(2):440-448.
12. Loo B W, Schuler E, Lartey F M, Rafat M, King G J, Trovati S, et al (2017). Delivery of ultra-rapid flash radiation therapy and demonstration of normal tissue sparing after abdominal irradiation of mice. Int. J. Rad. Onc. Biol. Phys. 98:E16.
13. Levy K, Natarajan S, Wang J, Chow S, Eggold J, Loo P, et al (2019). FLASH irradiation enhances the therapeutic index of abdominal radiotherapy in mice. bioRxiv [Prepint]. doi: 10.1101/2019.12.12.873414.
14. Simmons D A, Lartey F M, Schüler E, Rafat M, King G, Kim A, et al (2019). Reduced cognitive deficits after FLASH irradiation of whole mouse brain are associated with less hippocampal dendritic spine loss and neuroinflammation. Radiother. Oncol. 139:4-10.
15. Montay-Gruel P, Petersson K, Jaccard M, Boivin G, Germond J F, Petit B, et al (2017). Irradiation in a flash: unique sparing of memory in mice after whole brain irradiation with dose rates above 100 Gy/s. Radiother. Oncol. 124:365-9.
16. Bourhis J, Montay-Gruel P, Goncalves Jorge P, Bailat C, Petit B, Ollivier J, et al (2019). Clinical translation of FLASH radiotherapy: why and how? Radiother. Oncol. 139:11-7.
17. Hendry J H, Moore J V, Hodgson B W, Keene J P (1982). The constant low oxygen concentration in all the target cells for mouse tail radionecrosis. Radiat. Res. 92:172-81.
18. Field S B, Bewley D K (1974). Effects of dose-rate on the radiation response of rat skin. Int. J. Radiat. Biol. Relat. Stud. Phys. Chem. Med. (1974) 26:259-67.
19. Bourthis J, et al (2019). Treatment of a first patient with FLASH-radiotherapy. Radiother. Oncol. 139:18-22.
20. FLASH Therapy—Current status and the way to the clinic; SAM Therapy Scientific Symposium, AAPM annual meeting 2020.
21. FLASH Therapy with Protons—Dosimetry, Safety and Experimental Evidence, Scientific Panel 07, ASTRO annual meeting 2019,
22. FLASH Radiation—how it works (TR8); FLASH and other high intensity radiation (S28), Scientific sessions, Radiation Research Annual Meeting 2019, 23. Jaccard M, Duran M T, Petersson K, Germond J F, Liger P, Vozenin M C, Bourhis J, Bochud F, Bailat C (2017). High dose-per-pulse electron beam dosimetry: Commissioning of the Oriatron eRT6 prototype linear accelerator for preclinical use. Med. Phys. 45(2):863-874.

24. Schuler E, et al (2017). Experimental platform for ultra-high dose rate FLASH irradiation of small animals using a clinical linear accelerator. Int. J. Rad. Onc. Biol. Phys. 97(1): 195-203.

25. Patriarca A, et al (2018). Experimental set-up for FLASH proton irradiation of small animals using a clinical system. Int. J. Rad. Onc. Biol. Phys. 102(3):619-626.

26. Colangelo N W, Azzam EI (2020). The importance and clinical implications of FLASH ultra-high dose-rate studies for proton and heavy ion radiotherapy. Rad. Res. 193(1): 1-4.

27. Spitz D R, et al (2019). An integrated physico-chemical approach for explaining the differential impact of FLASH versus conventional dose rate irradiation on cancer and normal tissue responses. Radiother. Oncol. 139: 23-27, 28. Wilson P, Jones B, Yokoi T, Hill M, Vojnovic B (2012). Revisiting the ultra-high dose rate effect: implications for charged particle radiotherapy using protons and light ions. Brit. J. Radiol. 85: e933-e939.

29. Karsch L, et al (2017). Toward ion beam therapy based on laser plasma accelerators. Acta Oncologica 56(11): 1359-1366.

30. Buonanno M, Grilj V, Brenner D J (2019). Biological effects in normal cell exposed to FLASH dose rate protons. Radiother. Oncol. 139:51-55.

31. Durante M, Brauer-Krisch E, Hill M (2018). Faster and safer? FLASH ultra-high dose rate in radiotherapy. Br. J. Radiol. 91:20170628.

32. Maxim P G, Tantawi S G, Loo B W (2019). PHASER: A platform for clinical translation of FLASH cancer radiotherapy. Radiother. Oncol. 139:28-33.

33. Bazalova-Carter M, Esplen N (2019). On the capabilities of conventional x-ray tubes to deliver ultra-high (FLASH) dose rates. Med. Phys. 46(12): 5690-5696.

34. RAD-44 rotating anode x-ray tube, Varex Imaging Corp., Salt Lake City, UT. Catalog No. 133785-000 Rev A. https://www.vareximaging.com/sites/default/files/datasheets/vic/RAD-44pds_0.pdf 35. Beyreuther E, Karsch L, Laschinsky L, LeBmann E, Naumburger D, Oppelt M, et al (2015). Radiobiological response to ultra-short pulsed megavoltage electron beams of ultra-high pulse dose rate. Int. J. Radiat. Biol. (2015) 91:643-52.

36. Sharma R, Dutt Sharma S, Pawar S, Chaubey A, Kantharia S, Babu DAR (2015). Radiation dose to patients from X-ray radiographic examinations using computed radiography imaging system. J. Med. Phys. 40(1): 29-37.

37. Sungita Y Y, Mdoe SSL, Msaki P (2006). Diagnostic X-ray facilities as per quality control performances in Tanzania. J. Appl. Clinic. Med. Phys. 7(4): 66-73.

38. National Council on Radiation Protection and Measurement (U.S.). NCRP report No. 99 (1997). Quality assurance for diagnostic imaging equipment.

39. Ma C M, Coffey C W, DeWard L A, Liu C, Nath R, Seltzer S M, Seuntjens J P (2001). AAPM protocol for 40-300 kV x-ray beam dosimetry in radiotherapy and radiobiology. Med. Phys. 28(6): 868-893.

40. Ramish Ashraf M, Rahman M, Zhang R, Williams B B, Gladstone D J, Pogue B W, Bruza P (2020). Dosimetry for FLASH Radiotherapy: A Review of Tools and the Role of Radioluminescence and Cherenkov Emission. Front. Phys. 8 (328): 1-20.

41. Jaccard M, Petersson K, Buchillier T, Germond J F, Durin M T, Vozenin M C, et al (2017). High dose-per-pulse electron beam dosimetry: usability and dose-rate independence of EBT3 Gafchromic films. Med. Phys. 44: 725-35.

42. Agostinelli S, et al (2003). GEANT4—a simulation toolkit. Nucl. Instrum. Methods. Phys. Res. B. 506(3): 250-303.

43. Bordage M C, Bordes J, Edel S, Terrissol M, Franceries X, Bardies M, Lampe N, Incerti S (2016). Implementation of new physics models for low energy electrons in liquid water in Geant4-DNA. Physica Medica. 32(12): 1833-40.

44. Pandola L, Andenna C, Caccia B (2018). Validation of GEANT4 simulation of bremsstrahlung from thick targets below 3 MeV. Nucl. Instrum. Methods. Phys. Res. B. 350(1): 41-48.

45. Patallo I S, et al (2020). Development and Implementation of anEnd-To-End Test for Absolute Dose Verificationof Small Animal Preclinical Irradiation Research Platforms. Int. J. Rad. Onc. Biol. Phys. 107(3): 587-596.

46. Wang Y F, Lin S C, Na Y H, Black P J, Wuu C S (2018). Dosimetric verification and commissioning for a small animal image-guided irradiator. Phys. Med. Biol. 63:145001.

47. Bell B I, Koduri S, Salinas C S, Monslow J, Pure E, Ben-Josef E, Koumenis C, Verginadis II (2019). Interleukin 6 Signaling Blockade Exacerbates Acute and Late Injury From Focal Intestinal Irradiation. Int. J. Rad. Onc. Biol. Phys. 3(1): 719-727.

48. Verginadis I I, Kanade R, Bell B I, Koduri S, Ben-Josef E, Koumenis C (2017). A Novel Mouse Model to Study Image-Guided, Radiation-Induced Intestinal Injury and Preclinical Screening of Radioprotectors. Cancer Res. 77(4): 908-917.

49. Kim K K, et al (2009). Epithelial cell alpha3beta1 integrin links beta-catenin and Smad signaling to promote myofibroblast formation and pulmonary fibrosis. The Journal of clinical investigation 119, 213-224.

50. Kim K K, et al (2006). Alveolar epithelial cell mesenchymal transition develops in vivo during pulmonary fibrosis and is regulated by the extracellular matrix. Proceedings of the National Academy of Sciences of the United States of America 103, 13180-13185.

51. Wei Y. et al (2005). Regulation of alpha5beta1 integrin conformation and function by urokinase receptor binding. The Journal of cell biology 168, 501-511.

52. Kim K K, & Chapman H A (2007). Endothelin-1 as Initiator of Epithelial-Mesenchymal Transition: Potential New Role for Endothelin-1 during Pulmonary Fibrosis. American journal of respiratory cell and molecular biology 37, 1-2.

53. Hendry J H, Moore J V, Hodgson B W, Keene J (1982). The Constant Low Oxygen Concentration in All the Target Cells for Mouse Tail Radionecrosis. Rad Res, 92: 117-181.

54. Festing M F W, Altman D G (2002). Guidelines for the Design and Statistical Analysis of Experiments Using Laboratory Animals. ILAR J, 43(4): 244-258.

We claim:

1. An x-ray irradiation system, comprising:

a first x-ray tube constructed and arranged to be able to irradiate an object with at least a portion of a first x-ray beam emitted from said first x-ray tube;

a second x-ray tube constructed and arranged to be able to irradiate said object with at least a portion of a second x-ray beam emitted from said second x-ray tube simultaneously with said first x-ray beam and a positioning assembly to which the first and second x-ray tubes are attached, wherein first and second x-ray tubes are further arranged at respective first and second vertical positions on the positioning assembly, wherein said first and second x-ray tubes are arranged such that said first and second x-ray beams are incident on, and intersect within, the object at respective first and second oblique angles to define a target volume such that a dose rate is substantially uniform as prescribed within said target volume, and wherein the angle of at least one x-ray source is adjustable on the positioning assembly to irradiate the treatment volume with an x-ray beam at a range of angles from −90 to 90 degrees, as measured from a vertical axis parallel to the vertical structure.

2. The system of claim 1, wherein the vertical position of at least one x-ray tube is adjustable on the positioning assembly to irradiate the treatment volume with an x-ray beam at a range of source to surface distances (SSDs) from zero to 250 millimeters (mm), as measured from a surface of the object to the aperture of the x-ray tube.

3. The system of claim 2, wherein based on the vertical position and angle of at least one x-ray tube, the dose rate in the target volume is an ultra-high dose rate between 40 Gy/sec to 200 Gy/sec.

4. The system of claim 3, wherein at least one of the x-ray tubes comprises a rotating anode.

5. The system of claim 3, wherein at least one of the x-ray tubes is actively cooled.

6. The system of claim 2, wherein based on the vertical position and angle of at least one x-ray tube, the dose rate in the target volume is a conventional dose rate between 0.02 Gy/sec to 0.4 Gy/sec.

7. The system of claim 2, wherein based on the vertical position and angle of at least one x-ray tube, the dose rate in the target volume can be continually adjusted to achieve between 0.02 Gy/sec to 200 Gy/sec.

8. The system of claim 1 further comprising a sample holder positioned between the first x-ray tube and the second x-ray tube.

9. The system of claim 8, wherein the object is positioned within the sample holder.

10. The system of claim 9, wherein the object is a biological sample.

11. The system of claim 9, wherein the object is a living animal.

12. The system of claim 1, wherein the x-ray tubes are arranged in a mirrored orientation to minimize an inherent non-uniform emission of x-rays from each x-ray tube.

13. The system of claim 1 further comprising a filter coupled to an aperture of each x-ray tube, said filter configured to modify at least one of energy spectrum, flatness, and symmetry of the emitted x-ray beams.

14. The system of claim 13, wherein said filter is constructed of at least one of aluminum, beryllium, tin, copper, brass, tungsten, and alloys.

15. The system of claim 1 further comprising a collimator coupled to an aperture of each x-ray tube, said collimator configured to shape the x-ray beam during irradiation of the target volume.

16. The system of claim 1 further comprising a non-transitory machine-readable medium storing a set of instructions for performing Monte Carlo-based dose calculations of the irradiated target volume, said calculations comprising calculating at least one of delivered dose, dose rate, Linear Energy Transfer (LET) distribution, and distribution of chemical radicals.

17. The system of claim 1 further comprising a third x-ray tube constructed and arranged to be able to irradiate said object with at least a portion of a third x-ray beam emitted from said third x-ray tube simultaneously with said first and second x-ray beams, wherein said third x-ray tube is arranged such that said third x-ray beam is incident on, and intersects, said first and second x-ray beams within the object at a third oblique angle to further define the target volume such that the dose rate is substantially uniform within said target volume.

18. The system of claim 1, wherein at least one x-ray tube is operated at a max peak voltage between 50 kilovolts (kV) and 320 kV.

19. The system of claim 1, wherein at least one x-ray tube is operated at a current between 5 milliamperes (mA) and 1000 mA.

20. The system of claim 1, wherein at least one x-ray tube is operated for an exposure time between 50 milliseconds (msec) and 500 msec.

21. The system of claim 1 further comprising a self-shielded cabinet with an environmental control system.

22. The system of claim 1, wherein at least one x-ray tube is one of a radiographic x-ray tube, a fluoroscopic x-ray tube, an angiographic x-ray tube, and a tomographic x-ray tube.

23. A method for x-ray irradiation, comprising:

arranging a first x-ray tube to irradiate an object with at least a portion of a first x-ray beam emitted from said first x-ray tube; and arranging a second x-ray tube to irradiate said object with at least a portion of a second x-ray beam emitted from said second x-ray tube simultaneously with said first x-ray beam, wherein said first and second x-ray tubes are arranged such that said first and second x-ray beams are incident on, and intersect within, the object at respective first and second oblique angles to define a target volume such that a dose rate is substantially uniform as prescribed within said target volume, wherein the first and second x-ray tubes are attached to a positioning assembly to which, wherein the first and second x-ray tubes are further arranged at respective first and second vertical positions on the positioning assembly, and wherein the angle of at least one x-ray source is adjustable on the positioning assembly to irradiate the treatment volume with an x-ray beam at a range of angles from −90 to 90 degrees, as measured from a vertical axis parallel to the vertical structure.

24. The method of claim 23, further comprising arranging at least one x-ray tube at a vertical position and angle relative to the object such that the dose rate in the target volume is an ultra-high dose rate between 40 Gy/sec to 200 Gy/sec.

25. The method of claim 23, further comprising arranging at least one x-ray tube at a vertical position and angle relative to the object such that the dose rate in the target volume is a conventional dose rate between 0.02 Gy/sec to 0.4 Gy/sec.

* * * * *